(12) United States Patent
Pamplin et al.

(10) Patent No.: US 11,707,405 B2
(45) Date of Patent: Jul. 25, 2023

(54) COMPRESSION GARMENT

(71) Applicant: Koya, Inc., San Francisco, CA (US)

(72) Inventors: John C. Pamplin, San Francisco, CA (US); Gregory Biggers, San Francisco, CA (US)

(73) Assignee: Koya Medical, Inc., Oakland, CA (US)

( * ) Notice: Subject to any disclaimer, the term of this patent is extended or adjusted under 35 U.S.C. 154(b) by 159 days.

(21) Appl. No.: 16/486,433

(22) PCT Filed: Feb. 16, 2018

(86) PCT No.: PCT/IB2018/050970
§ 371 (c)(1),
(2) Date: Aug. 15, 2019

(87) PCT Pub. No.: WO2018/150372
PCT Pub. Date: Aug. 23, 2018

(65) Prior Publication Data
US 2020/0000677 A1    Jan. 2, 2020

Related U.S. Application Data

(60) Provisional application No. 62/459,773, filed on Feb. 16, 2017.

(51) Int. Cl.
*A61H 23/02* (2006.01)
*A61H 11/00* (2006.01)
*A61F 13/08* (2006.01)

(52) U.S. Cl.
CPC .......... *A61H 23/02* (2013.01); *A61F 13/085* (2013.01); *A61H 2011/005* (2013.01);
(Continued)

(58) Field of Classification Search
None
See application file for complete search history.

(56) References Cited

U.S. PATENT DOCUMENTS

| 4,018,064 A | 4/1977 | Doslik |
| 4,527,402 A | 7/1985 | Swallow et al. |

(Continued)

FOREIGN PATENT DOCUMENTS

| CN | 101098670 B | 7/2011 |
| CN | 103941909 A | 7/2014 |

(Continued)

OTHER PUBLICATIONS

International Search Report in Application No. PCT/IB2018/050970, dated May 16, 2018 in 7 pages.

*Primary Examiner* — Bradley H Philips
*Assistant Examiner* — Savannah L Gabriel
(74) *Attorney, Agent, or Firm* — Knobbe, Martens, Olson & Bear, LLP

(57) ABSTRACT

In an embodiment, a compression garment can include one or more of a flex frame, a shape memory material, a backing, and a control module. In some variations, the flex frame can include a set of support regions, a set of cutout regions, a set of bridges, one or more terminals, and one or more rotation points. In some variations, the compression garment 100 can further include a fabric sleeve, one or more fasteners, a power module, and/or any other suitable component. The compression garment functions as a compression device (e.g., to improve circulation, enhance muscle recovery, etc.), and can additionally or alternatively function as a passive compression device, a heating and/or cooling device, or perform any other suitable functionality.

19 Claims, 13 Drawing Sheets

(52) U.S. Cl.
CPC ............... *A61H 2201/0207* (2013.01); *A61H 2201/0214* (2013.01); *A61H 2201/5058* (2013.01)

(56) References Cited

U.S. PATENT DOCUMENTS

| | | | |
|---|---|---|---|
| 5,787,732 | A | 8/1998 | Perron et al. |
| 5,996,205 | A | 12/1999 | Mashiko et al. |
| 5,997,465 | A | 12/1999 | Savage et al. |
| 6,123,681 | A | 9/2000 | Brown, III |
| 6,190,344 | B1* | 2/2001 | Bobroff ............... A61F 5/0102 602/21 |
| 6,509,094 | B1* | 1/2003 | Shah ............... A61M 25/0009 427/372.2 |
| 7,857,777 | B2 | 12/2010 | Larson et al. |
| 7,868,221 | B2 | 1/2011 | Munch-Fals et al. |
| 7,896,825 | B2 | 3/2011 | Atkinson et al. |
| 8,517,963 | B2 | 8/2013 | Larson et al. |
| 8,523,794 | B2 | 9/2013 | Iker et al. |
| 8,764,689 | B2 | 7/2014 | Toth |
| 9,027,408 | B2 | 5/2015 | Toth |
| 9,161,878 | B1* | 10/2015 | Pamplin ............... A61H 7/001 |
| 9,248,074 | B2 | 2/2016 | Toth |
| 9,271,676 | B2 | 3/2016 | Alanen et al. |
| 9,271,890 | B1 | 3/2016 | Pamplin et al. |
| 9,326,911 | B2 | 5/2016 | Wyatt et al. |
| 9,463,821 | B1 | 10/2016 | Critchley et al. |
| 9,516,923 | B2 | 12/2016 | Capra et al. |
| 9,555,935 | B2 | 1/2017 | Fiedler |
| 9,572,410 | B2 | 2/2017 | Fiedler |
| 9,677,581 | B2 | 6/2017 | Tucholke et al. |
| 9,700,102 | B2 | 7/2017 | McCleary et al. |
| 9,907,367 | B2 | 3/2018 | Paik et al. |
| 9,936,772 | B2 | 4/2018 | Paik |
| 10,071,012 | B2 | 9/2018 | Larson et al. |
| 10,085,521 | B2 | 10/2018 | Chen et al. |
| 10,098,422 | B2 | 10/2018 | Fiedler et al. |
| 10,111,500 | B2 | 10/2018 | Lambert |
| 10,143,270 | B2 | 12/2018 | Fiedler et al. |
| 10,188,152 | B2 | 1/2019 | Stasey et al. |
| 10,206,461 | B1 | 2/2019 | Swetish |
| 10,285,902 | B2 | 5/2019 | Pamplin et al. |
| 10,307,074 | B2 | 6/2019 | Ward |
| 10,426,202 | B2 | 10/2019 | Wyatt et al. |
| 10,441,491 | B2 | 10/2019 | Wyatt et al. |
| 10,617,593 | B2 | 4/2020 | Wyatt et al. |
| 10,668,305 | B2 | 6/2020 | Cheatham, III et al. |
| 10,688,007 | B2 | 6/2020 | Wyatt et al. |
| 10,743,621 | B2 | 9/2020 | Wyatt et al. |
| 2002/0156401 | A1 | 10/2002 | Sherman et al. |
| 2003/0005558 | A1 | 1/2003 | Wong |
| 2005/0043657 | A1 | 2/2005 | Couvillon, Jr. |
| 2010/0234779 | A1 | 9/2010 | Asvadi et al. |
| 2011/0139835 | A1 | 6/2011 | Fikes |
| 2011/0189444 | A1 | 8/2011 | Beers |
| 2012/0065561 | A1 | 3/2012 | Ballas et al. |
| 2012/0101417 | A1* | 4/2012 | Joseph ............... A61F 5/058 602/5 |
| 2012/0232447 | A1 | 9/2012 | Gordon et al. |
| 2013/0030335 | A1* | 1/2013 | Norton ............... A61H 7/001 601/84 |
| 2013/0267995 | A1 | 10/2013 | Voss et al. |
| 2013/0303957 | A1 | 11/2013 | Bauerfeind |
| 2014/0081187 | A1 | 3/2014 | Wyatt et al. |
| 2015/0025426 | A1 | 1/2015 | Larson et al. |
| 2015/0065930 | A1 | 3/2015 | Wyatt |
| 2015/0073318 | A1* | 3/2015 | Holschuh ............... B64G 6/00 601/84 |
| 2015/0073319 | A1 | 3/2015 | Holschuh et al. |
| 2016/0022528 | A1 | 1/2016 | Wyatt et al. |
| 2016/0074234 | A1 | 3/2016 | Abichandani et al. |
| 2016/0120733 | A1 | 5/2016 | Ishikawa et al. |
| 2016/0175179 | A1 | 6/2016 | Pamplin et al. |
| 2016/0193100 | A1 | 7/2016 | Toth |
| 2016/0220808 | A1 | 8/2016 | Hyde et al. |
| 2016/0331620 | A1* | 11/2016 | Kazanchyan ........ A61N 1/3603 |
| 2016/0374886 | A1* | 12/2016 | Wyatt ............... A61H 7/007 601/18 |
| 2017/0196347 | A1 | 7/2017 | Sawhney et al. |
| 2017/0246073 | A1 | 8/2017 | Van-De-Velde |
| 2017/0252252 | A1 | 9/2017 | Wyatt et al. |
| 2017/0304136 | A1* | 10/2017 | Holschuh ............... A41D 31/00 |
| 2017/0304139 | A1 | 10/2017 | Ross |
| 2017/0312161 | A1* | 11/2017 | Johnson ............... A61F 5/0123 |
| 2018/0055009 | A1 | 3/2018 | Wyatt et al. |
| 2018/0125173 | A1 | 5/2018 | Lambert |
| 2018/0177677 | A1 | 6/2018 | Pamplin et al. |
| 2018/0192745 | A1 | 7/2018 | McDaniel |
| 2018/0214616 | A1 | 8/2018 | Muschalek et al. |
| 2018/0242655 | A1 | 8/2018 | Holschuh et al. |
| 2019/0274372 | A1 | 9/2019 | Rizzo et al. |
| 2020/0000676 | A1 | 1/2020 | Pamplin et al. |
| 2020/0154804 | A1 | 5/2020 | Huang |
| 2021/0386614 | A1 | 12/2021 | Doraiswamy et al. |
| 2022/0022606 | A1 | 1/2022 | Doraiswamy et al. |

FOREIGN PATENT DOCUMENTS

| | | |
|---|---|---|
| CN | 105082129 A | 11/2015 |
| CN | 105804960 | 7/2016 |
| KR | 10-1569850 | 11/2015 |
| WO | WO 2013/025481 | 2/2013 |
| WO | WO 2013/149985 | 10/2013 |
| WO | WO 2014/172248 | 10/2014 |
| WO | WO 2016/048827 | 3/2016 |
| WO | WO 2016/077150 | 5/2016 |
| WO | WO 2017/027145 | 2/2017 |
| WO | WO 2018/013188 | 1/2018 |
| WO | WO 2018/150372 | 8/2018 |
| WO | WO 2020/144437 | 7/2020 |
| WO | WO 2021/252770 | 12/2021 |
| WO | WO 2022/020370 | 1/2022 |

* cited by examiner

COMPRESSION GARMENT

CROSS-REFERENCE TO RELATED APPLICATIONS

This application is the U.S. National Phase under 35 U.S.C. § 371 of International Application No. PCT/IB2018/050970, filed Feb. 16, 2018, which claims the benefit as a nonprovisional application of U.S. Provisional Application No. 62/459,773 filed on Feb. 16, 2017, which is hereby incorporated by reference in its entirety.

TECHNICAL FIELD

This invention relates generally to the active compression field, and more specifically to a new and useful compression garment in the active compression field.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
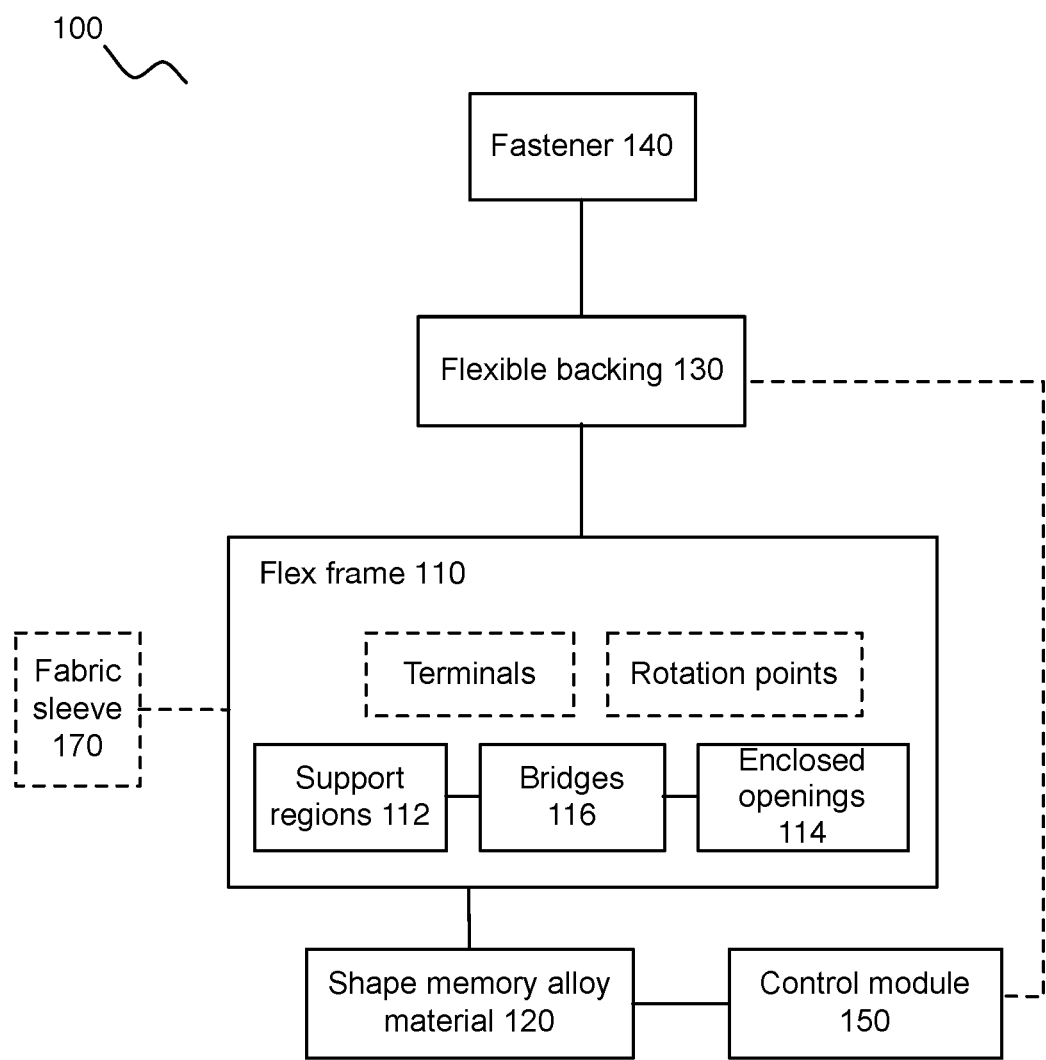
FIG. 1 is a schematic representation of an embodiment of the compression garment.

As shown in FIG. 1, an embodiment of the compression garment 100 includes: a flex frame 110, a shape memory (SM) material 120, a flexible backing 130, and a control module 140. In some variations (e.g., FIGS. 2, 4A-4B, and 5A-5B), the flex frame 110 can include a set of support regions 112, a set of cutout regions 114, a set of bridges 116, one or more terminals 118, and one or more rotation points 119. In some variations, the compression garment 100 can further include a fabric sleeve 105, one or more fasteners 150, a power module 160, and/or any other suitable component. The compression garment functions as an active compression device (e.g., to improve circulation, enhance muscle recovery, etc.), and can additionally or alternatively function as a passive compression device, a heating and/or cooling device, or perform any other suitable functionality.

2. Benefits.

There are numerous scenarios in which compression applied to the body is beneficial. Various medical conditions, for instance, such as deep vein thrombosis, lymphedema, blood clots, venous ulcers, venous insufficiency, varicose veins, as well as general swelling and circulation issues, can benefit from applied compression. Applied compression can also be beneficial for athletes, as it can assist with muscle recovery, among other uses. Active compression, in particular, can be particularly efficacious. Most devices that apply active compression, however, use pneumatic technology to apply the compression, and therefore tend to be big, bulky, and non-portable. The inventors have discovered that using shape memory material in combination with a flex frame can provide appropriate levels of active compression using a lightweight and portable garment. This provides the benefits not only of user comfort but also user mobility (e.g., can wear the compression garment while driving, in the office, sleeping, etc.).

3. System.

As shown in FIG. 1, the compression garment includes a flex frame 110, a shape memory (SM) material 120, a flexible backing 130, and a control module 140. In some variations (e.g., FIGS. 2, 4A-4B, and 5A-5B), the flex frame 110 can include a set of support regions 112, a set of cutout regions 114, a set of bridges 116, one or more terminals 118, and one or more rotation points 119. In some variations, the compression garment 100 can further include a fabric sleeve 105, one or more fasteners 150, a power module 160, and/or any other suitable component.

3.1 System—Flex Frame

The flex frame 110 functions to support other system elements and to apply active compression to a user (e.g., to a limb of a user) by changing morphologically (e.g., in length or another dimension) based on a change in current and/or temperature and/or other parameter applied to active system elements. Additionally or alternatively, the flex frame 110 can function to apply passive compression to a user, contract and/or extend in length (e.g., based on the configuration of an SM material), restore an SM material (e.g., SM polymer, shape memory alloy) to an initial configuration, and/or perform any other suitable function.

The flex frame can be an elongated member (e.g., a strip), but can additionally or alternatively include a series of shorter elements connected together, a sleeve, a patch, and/or any other element having any suitable geometry. The flex frame can define a first broad surface and a second broad surface opposing the first broad surface (e.g., in relation to surfaces oriented toward the body of the user or away from the body of the user during use). In one variation, the flex frame is wrapped circumferentially around a limb of a user (e.g., a leg of the user), with the first broad surface oriented toward the user.

Figure 6A:
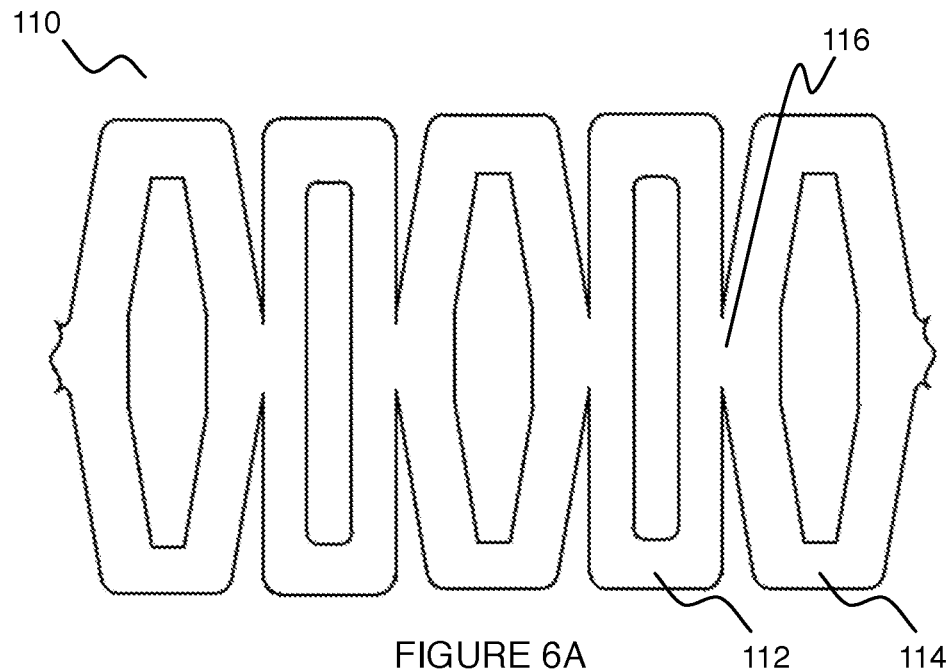
FIGS. 6A and 6B are example embodiments of a flex frame in an extended state and in a contracted state, respectively.
Figure 6B:
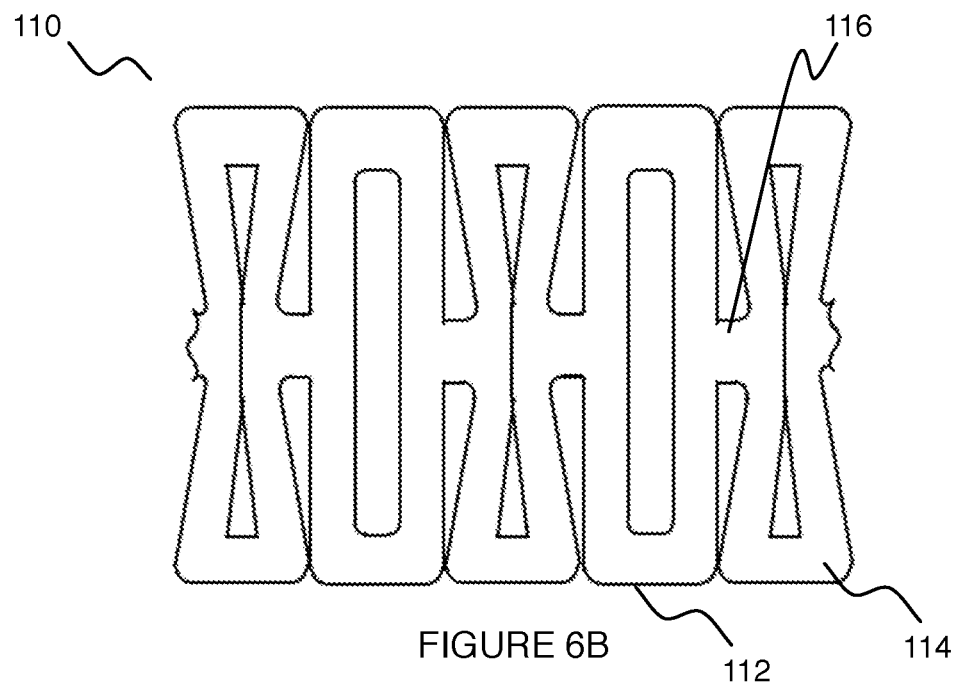

The flex frame is preferably constructed from plastic (e.g., a thermoplastic), but can additionally or alternatively be constructed from rubber, silicone, fabric (e.g., elastic), foam, metal, wood, or any other suitable material. The flex frame is preferably configured to be any or all of: flexible, capable of changing morphologically (at least in some portions) in a repeatable manner, and capable of supporting a shape memory material. Additionally or alternatively, the flex frame can be configured for any other suitable function. The flex frame 110 is preferably constructed, at least in part, from a material having properties which enable the flex frame to both morphologically change (e.g., expand and contract in length) and to support a SM material (e.g., one or both of an SM alloy and an SM polymer, combinations/composites of SM materials, etc.) array coupled to the flex frame. In one variation, the flex frame extends and contracts in length, as shown in FIGS. 6A and 6B respectively, due to the morphological changes of an SM material (e.g., SM alloy). As such, the flex frame 110 can be composed of one or more materials having a material property (e.g., stiffness, compliance, flexibility, elasticity, deformability, etc.) within a specified range of values (e.g., elastic modulus less than 3 GPa, elastic modulus between 0.01 and 2 GPa, elastic modulus between 0.1 and 1 GPa, etc.). The elastic deformation of the flex frame is preferably within a range of dimensional changes in a SM material of the compression garment, such that the flex frame is not subject to plastic deformation in normal use. Additionally or alternatively, the flex frame can be constructed from a relatively high stiffness material (e.g., a material that retains a characteristic length of the flex frame in response to a range of applied forces), a relatively low stiffness material, or any other suitable material or combination of materials. In one variation, the flex frame 110 is physically coextensive and/or of unitary construction (e.g., constructed from a single material). In alternative variations, the flex frame 110 can be constructed from multiple materials, such as two or more materials having different stiffnesses (e.g., different elastic moduli), or multiple pieces (e.g., multiple pieces of the same material). The flex frame can be constructed using any or all of: injection molding, vacuum forming, die cutting, laser cutting, 3D printing, and/or any other process(es). Portions of the flex frame can be joined together through the use of adhesives, heat sealing, sewing, fasteners, and/or any other suitable element or process.

Preferably, the compression garment includes multiple flex arrays (e.g., set of flex frames 110) arranged along a proximal-distal axis of a limb of the user during use. In one variation, for instance, a series of flex arrays is arranged along a proximal-distal axis (e.g., along the length) of a leg to span the length of the calf. Additionally or alternatively, a series of flex arrays can be arranged along a medial-lateral axis relative to any body region of the user during use. In one variation, for instance, a series of flex arrays can be layered over each other; this can, for instance, function to enhance compressive effects (e.g., provide a higher achievable level of applied compression) of the device. Additionally or alternatively, a series of flex frames can be arranged circumferentially (e.g., in a row) about a body region of a user during use. In one example of this variation, a compression garment for a limb of varying diameter can have multiple flex arrays arranged about the limb during use (e.g., in a row at the areas of the limb having a larger diameter relative to other areas of the limb). Further additionally or alternatively, any number of flex arrays can be arranged in any suitable configuration (e.g., along an inferior-superior direction during use, along an anterior-posterior direction during use, along any other suitable direction during use).

In one variation, the flex frame 110 is configured to restore a SM material to an initial (e.g., relaxed) configuration. In a specific example, the flex frame is encased in an SM polymer (e.g., polymer foam), wherein the flex frame is configured to (e.g., by having a spring constant within a predetermined range of values) restore the SM polymer foam a compressed state to an expanded state. In a second specific example, an SM alloy (e.g., SM alloy wire) is at least partially encased in an SM polymer sleeve, wherein the SM polymer sleeve contracts due to heat generated by the SM alloy and wherein the flex frame serves to restore to the SM polymer to an extended/expanded state.

In a second variation, the flex frame 110 is constructed from an SM material (e.g., SM polymer). In a specific example, the flex frame 110 is an SM polymer sheet.

3.2 System—Support Region

Preferably, the flex frame 110 includes one or more support regions 112. The support regions 112 function to support SM material, such as through holding, retaining, securing, or otherwise supporting the SM material. Additionally or alternatively, the support regions 112 can function to resist compression (e.g., act as a strut) or otherwise contribute rigidity to the flex frame.

Preferably, the support regions 112 are arranged on a broad surface (e.g., the first broad surface) of the flex frame 110. Additionally or alternatively, support regions 112 can be arranged on multiple broad surfaces (e.g., the first and second broad surface), elsewhere on the flex frame, through an interior portion of the flex frame between the first broad surface and the second broad surface, or connected to a separate element (e.g., a fabric sleeve, flexible backing, etc.) of the compression garment.

Each support region 112 preferably includes a protruding region, the protruding region having a greater thickness than the thickness of the flex frame immediately adjacent (e.g., bordering) the protruding region. Additionally or alternatively, the protruding region can have a thickness equal to or less than the thickness of the adjacent flex frame. The protruding region, for instance, can be offset (e.g., elevated) from the flex frame. Additionally or alternatively, each support region can include one or more of: a ridge, hook, through-hole, adhesive, magnet, tab, or other mechanism for supporting (e.g., retaining) SM material.

Each support region 112 is preferably constructed from the same material as the rest of the flex frame. Additionally or alternatively, the support region 112 can be partially or fully constructed from material having a higher stiffness than another region of the flex frame, a lower stiffness than another region of the flex frame, different ferromagnetic properties, different surface properties (e.g., textured surface), or any other material properties. Further additionally or alternatively, the support region 112 can be constructed from multiple materials (e.g., metal and plastic). Preferably, each support region 112 is constructed from material having a material property (e.g., stiffness) above a predetermined threshold (e.g., elastic modulus above 0.01 GPa, elastic modulus above 0.1 GPa, elastic modulus above 1 GPa, etc.) but can additionally or alternatively have a material property below a predetermined threshold, a material property within a predetermined range of values, a material property that changes (e.g., a thermoplastic), or any other set of material properties.

Preferably, the flex frame includes a series of support regions 112 arranged along the length of the flex frame but can alternatively include a single support region (e.g., a continuous support region running along the center of the flex frame). Preferably, in the case of a series of support regions 112, there is a fixed spacing between neighboring support regions along the length of the flex frame; additionally or alternatively, there can be multiple spacing values between neighboring support regions 112, a random arrangement of support regions 112, or any other arrangement of a series of support regions 112.

In a first variation, the support region 112 includes a protruding region having a groove. In a specific example, for instance, the support region 112 can be a protruding region having a greater thickness than the rest of the flex frame, wherein the protruding region has grooves spaced at opposite ends of a short dimension of the flex frame (e.g., vertically, in the orientation shown in FIG. 4B). The grooves can be offset from each other along the thickness of the protruding region (e.g., to minimize friction between SM material arranged in grooves) or along any other direction of the protruding region. In another example of the first variation, the support region can have a groove running all the way around a protruding region. In these variations, SM material can be wound around support regions and/or between a series support regions. In one example, for instance, SM wire can be arranged between opposite ends of adjacent support regions (e.g., pass from a first end of a first support region to a second end of a second support region to a first end of a third support region, etc.); this arrangement can be seen in FIG. 4B. In another example, the SM wire can be arranged between the same ends of adjacent support regions (e.g., pass from a first end of a first support region to a first end of a second support region to a first end of a third support region, etc.).

In a second variation, the support region 112 includes one or more through-holes to retain SM material. In one example, the support region 112 can have a uniform thickness with the rest of the flex frame and a series of through-holes through the thickness, wherein SM material is laced through the through-holes. In another example, a support region 112 having a protruding region can have through-holes through an edge (e.g., in a direction orthogonal to the direction of the thickness) of the protruding region, wherein the SM material passes through the edge through-holes.

In a third variation, the support region can include magnetic guides to retain SM material. In one example, for instance, a groove of the support region can receive a magnetic insert which functions to attract SM material (e.g., a SM wire with a magnetic coating).

3.3 System—Enclosed Openings

The flex frame 110 preferably includes one or more enclosed openings 114, which function to morphologically change (e.g., provide flexibility to allow for contractions and/or extensions in a bulk length of the flex frame 110) in response to morphological changes to the SM material. Additionally or alternatively, each of the enclosed openings 114 can function to reduce the total material of the flex frame and/or compression garment, which can contribute to making the compression garment lightweight and/or portable.

Preferably, the enclosed openings 114 include one or more cutouts through a broad surface of the flex frame. Additionally or alternatively, the enclosed openings 114 can be through any surface of the flex frame. The flex frame 110 preferably includes a series of enclosed openings 114 arranged in an alternating fashion with a series of support regions 112. Additionally or alternatively, a set of enclosed openings 114 can be arranged adjacent to each other, biased toward one or more ends of the flex frame 110, biased toward the center of the flex frame 110, and/or arranged in any other sequence at any portion of the flex frame. In some variations, the arrangement of protruding regions 112 and enclosed openings 114 can be determined based on the dimensions and/or contours of a body part, interchangeable and/or moveable, selected by the user, or otherwise arranged. Preferably, the enclosed openings 114 are fully enclosed openings, wherein the entire opening 114 is bordered by a material of the flex frame. Additionally or alternatively, any or all the enclosed openings 114 can be partially enclosed.

The enclosed openings 114 preferably include rectangular cutouts (e.g., in an un-deformed configuration) but can additionally or alternatively include circular cutouts, ovate cutouts, slits, perforations, or any other suitable type and shape of opening to provide an appropriate response to changes in length of an SM material (e.g., in relation to providing appropriate compression characteristics at an intended position on a user's body, etc.). In some variations, the enclosed openings 114 can include a material (e.g., an insulative material) within, in front of, behind, or otherwise arranged in relation to the enclosed openings 114.

Preferably, the set of enclosed openings 114 is incorporated into the flex frame 110 at the time of manufacture of the flex frame (e.g., through injection molding). Additionally or alternatively, any or all of the enclosed openings 114 can be incorporated into the flex frame through a secondary process, such as a removal process (e.g., cutting, die-cutting, milling, etc.), or through any other suitable process or event.

In a first variation, each of a series of enclosed openings 114 includes an enclosed opening 114 through a broad surface of the flex frame, each enclosed opening 114 defined by a thin frame of material (e.g., a spring link). In a specific example, the flex frame 110 includes a series of elongated (e.g., along a proximal-distal axis of a limb) rectangular cutouts 114 surrounded by an elongated rectangular frame of flex frame material. In another specific example, the flex frame 110 includes a series of elongated (e.g., along a proximal-distal axis of a limb) cutouts 114 surrounded by an elongated frame of material, wherein the material of the frame surrounding the enclosed opening 114 is different (e.g., higher flexibility) and/or separate from the surrounding flex frame material. In this example, the outer perimeter of the frame surrounding the enclosed opening 114 can be attached to a protruding region 112 or another frame surrounding an enclosed opening 114 though a linkage, adhesive, heat treatment, stamping, or through any other mechanism.

In a second variation, the enclosed opening 114 can include a plurality of openings (e.g., perforations in the flex frame, slits in the flex frame, etc.). In this variation, the frame surrounding the enclosed opening 114 can be considered to be the material of the flex frame surrounding all of the perforations, a subset of the perforations, the entire flex frame, or any other material.

3.4 System—Bridges

Preferably, the flex frame 110 includes one or more bridges 116. The bridge 116 can function to connect a support region 112 and an enclosed opening 114. Additionally or alternatively, the bridge 116 can function to connect two support regions 112, connect two enclosed openings 114, connect two flex frames 110, increase or decrease a parameter (e.g., flexibility, compressibility, extension, contraction, stiffness, etc.) of the flex frame 110, reduce overall material of the flex frame, contribute to the device being lightweight and/or portable, or perform any other suitable function.

The bridge 116 is preferably rectangular with a smaller height (measured along a proximal-distal axis when the compression garment is placed on a limb of a user) than the height of the flex frame 110, the height of the protruding region 112, and the height of the enclosed opening 116. Additionally or alternatively, the height of the bridge 116 can be smaller, equal to, or larger than any or all of the mentioned heights. Further, the bridge 116 preferably has a smaller length (measured in a circumferential direction when the compression garment is placed on a limb of a user) than that of the flex frame 110, support region 112, and enclosed opening 116, but can additionally or alternatively have any suitable length. The bridge 116 preferably has the same thickness (measured in a direction orthogonal to a broad surface of the flex frame) as the frame of the enclosed opening 114 but can additionally or alternatively have the same thickness as the flex frame 110, the support region 112, or any other suitable thickness. Additionally or alternatively, the bridge 116 can be helical (e.g., a spring), cylindrical, or have any other configuration.

Each bridge 116 preferably physically coextensive and of unitary construction with the flex frame 110. Additionally or alternatively, the bridge 116 can be attached to the flex frame (e.g., through a fastener), or otherwise arranged in the flex frame. The bridge 116 is preferably constructed from a polymer (e.g., plastic, thermoplastic, rubber, etc.), metal, fabric (e.g., elastic) but can additionally or alternatively be constructed from any suitable material. In preferred variations, the bridge 116 is constructed from a material of the flex frame (e.g., the bridge is formed from injection molding of the flex frame), but can additionally or alternatively be constructed from any other suitable material.

Each flex frame 110 preferably includes a plurality of bridges 116 arranged along a length of the flex frame 110. The plurality of bridges can be arranged at a fixed spacing with respect to each other, biased toward one or more ends of the flex frame 110, biased toward the center of the flex frame 110, and/or arranged in any other way at any portion of the flex frame. Preferably, a bridge 116 is arranged between each enclosed opening 114 and an adjacent support region 112 but can additionally or alternatively be arranged between adjacent enclosed openings 114, adjacent support regions 112, a subset of any of these, or at any other location(s) of the flex frame 110.

In a first variation, the flex frame 110 includes a series of bridges 116, each of the series of bridges 116 arranged between an enclosed opening 114 and an adjacent support region 112, wherein each bridge 116 extends from an outer perimeter of the frame of the enclosed opening 114 to an outer perimeter of the support region 112. In a first specific example of this variation, each bridge is physically coextensive with and of unitary construction with the flex frame. In a second specific example of this variation, each bridge 116 is a helical spring (e.g., a metal spring) attached on one end to an outer perimeter of the enclosed opening frame and on the other end to an outer perimeter of the support region. In a third specific example, each bridge is a piece of fabric (e.g., a string, section of elastic, etc.).

In a second variation, the flex frame 110 includes a set of bridges arranged only at an end or ends of the flex frame 110. In a specific example, the flex frame 110 can include a bridge at each end configured to connect two flex frames together (e.g., in a circumferential arrangement). In another specific example, the flex frame 110 can include one or more bridges at a long edge of a broad surface of the flex frame, the bridges configured to connect two flex frames together (e.g., along a proximal-distal direction).

3.5 System—Terminals

The flex frame 110 preferably includes one more terminals 117, each of which can function to provide a site of electrical connection (e.g., for the SM material) to the flex frame. Additionally or alternatively, the terminal 117 can function to provide a site of mechanical connection (e.g., for the SM material) to the flex frame.

The terminal 117 preferably includes a conductive material (e.g., for electrical connection) but can additionally or alternatively include a non-conductive material (e.g., an insulative material for protection of user, a non-conductive material for mechanical connection, etc.). Preferably, the flex frame 110 includes two terminals but can additionally or alternatively include any number of terminals. Each terminal is preferably connected to a control module of the compression garment, but can additionally or alternatively be connected to a power module of the compression garment, any circuitry of the compression garment, or any other element of the compression garment. Each terminal 117 is preferably arranged in or through a broad surface of the flex frame 110, such that SM material can be connected to the terminal(s).

In one variation, the flex frame 110 includes two terminals arranged at opposing ends along the length of the flex frame 110, wherein a first end of an SM material attaches to the first terminal and a second end of an SM material attaches to the second terminal.

3.6 Rotation Points

The flex frame 110 can include one or more rotation points 118, wherein the rotation point 118 functions to allow rotation of a flex frame 110 in the compression garment. Additionally or alternatively, the rotation point 118 can function to connect multiple flex frames together, connect a flex frame to a flexible backing or to another element (e.g., a fastener) in the compression garment, support an SM material (e.g., retain to the flex frame 110), or perform any other suitable function.

Preferably, the rotation point 118 is physically coextensive with and of unitary construction with the flex frame 110. Additionally or alternatively, the rotation point 118 can be attached to the flex frame (e.g., with an adhesive), to a flexible backing or a fastener of the compression garment, or to any other element of the compression garment. Preferably, the rotation point 118 is located at an end of the flex frame 110, but can additionally or alternatively be located along the length (e.g., a series of rotation points arranged with a fixed spacing) of the flex frame 110, along an edge of the flex frame, or elsewhere in the compression garment. The rotation point 118 is preferably constructed from a material used elsewhere in the flex frame but can additionally or alternatively be constructed from a different material (e.g., metal). The rotation point 118 can include a protruding region, disk, hook, ball-and-socket joint, or any other feature. In one variation, the rotation point 118 has conductive properties to, for instance, serve as a terminal for SM material.

In a first variation, the rotation point supports an SM material. In a first specific example, the SM material (e.g., SM wire, SM ribbon, etc.) is wound or wrapped around at least a partial perimeter of the rotation point. In a second specific example, the SM material passes through rotation point 118 (e.g., a loop, hook, through-hole, etc.). In a third specific example, the rotation point 118 is adjacent (e.g., circumscribed by) a terminal 117.

3.7 Covering

Figure 7:
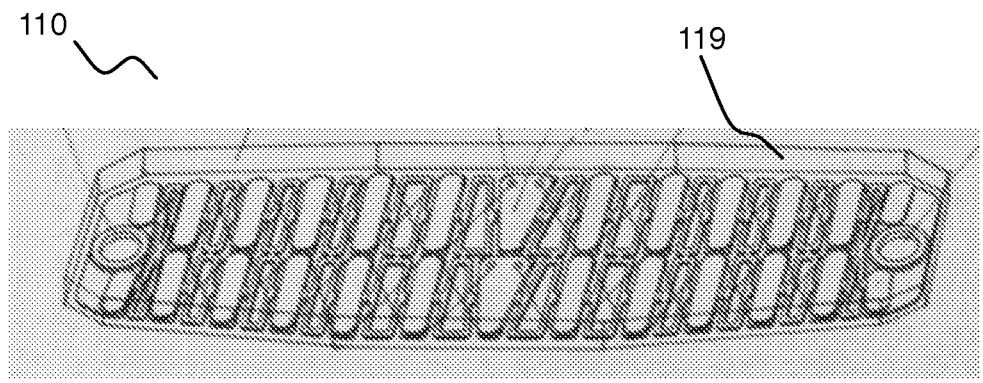
FIG. 7 is an example embodiment of a flex frame encased in an outer covering.

In some variations (e.g., FIGS. 7 and 8), the flex frame 110 further includes a covering (e.g., encasement) 119, which can function to enclose, insulate, support, or other cover at least part of the flex frame 110. The flex frame 110 can be mounted to (e.g., with adhesive) or embedded in the covering 119, but can additionally or alternatively be otherwise attached to the covering 119.

The covering 119 is preferably constructed from a soft and flexible material configured to, at least in part, transmit the morphological changes (e.g., compressions) of the flex frame 110 to a user. The covering 119 material can be a polymer, foam, fabric, or any other suitable material. In some variations, the covering 119 material is a shape memory foam or polymer. In other variations, the covering 119 is an insulating foam.

In a first variation, the covering 119 includes a heating element (e.g., an air-activated hand warmer), which functions to cause a morphological change (e.g., contraction) in an SM material.

In a second variation, the covering 119 includes an insulative material, which functions to protect a user from electronics of the compression garment and/or heat generated by the compression garment.

In a third variation, the covering 119 includes a cushioning material, which functions to provide comfort to a user.

Figure 8:
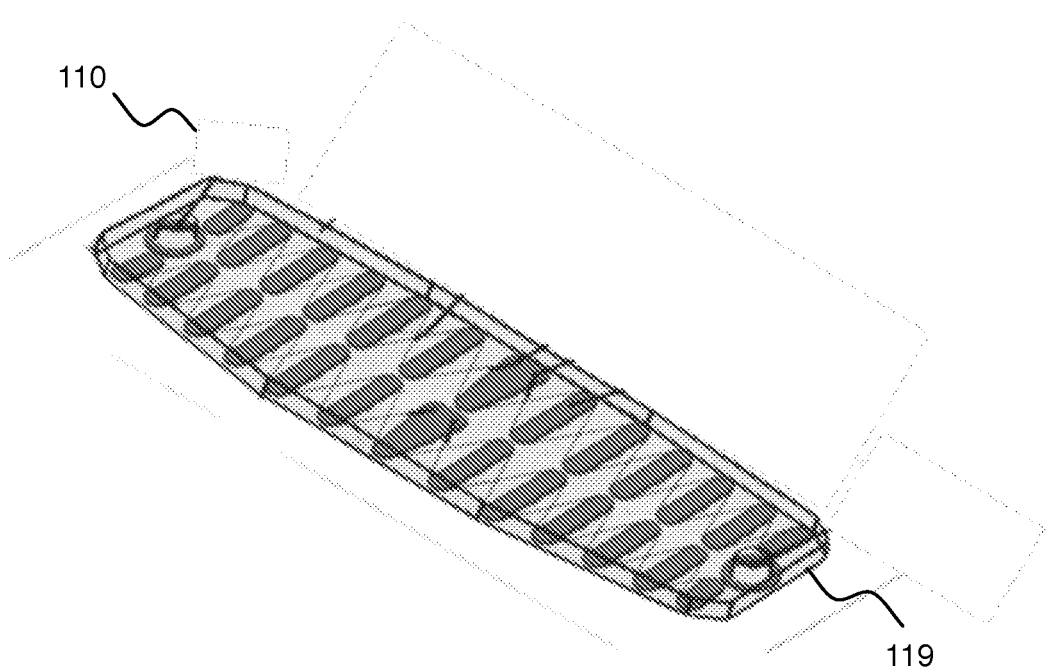
FIG. 8 is an example embodiment of a flex frame encased in an outer covering.

In a fourth variation, as seen in FIG. 8, the flex frame 110 can include only a series of support regions 112 mounted to or encased in an outer covering 119. In a specific example, the support regions 112 can be encased in a foam and collectively support an SM wire wrapped around grooves in one or more edges of the support regions 112.

In a fifth variation, the flex frame 110 includes a continuous sheet of SM material. In a specific example, the flex frame 110 includes an SM polymer sheet that is cut or molded to a specific size and shape to fit around a part of the user's body, such as a limb (e.g., calf). The SM polymer sheet can be attached to a fabric backing along one or more sides. It can also have rotation points at either end to connect to the attachment means. The SM polymer sheet can further have an internal flex frame. The sheet of SM polymer can be externally stimulated or internally stimulated (e.g., by an electric field, magnetic field, heat, UV radiation, or moisture).

3.8 System—Shape Memory (SM) Material

The compression garment 100 preferably includes an SM material 120, which can function to morphologically change (e.g., contract and/or lengthen) in response to a stimulus (e.g., applied current, temperature change). Additionally or alternatively, the SM material 120 can function to cause a morphological change (e.g., contraction, extension, compression, expansion, etc.) in the flex frame 110, flexible backing, and/or any other element in the compression garment. Further additionally or alternatively, the SM material 120 can function to connect components of the compression garment 100 together, such as flex frames 110, protruding regions 112, enclosed openings 114, or any other components.

The SM material 120 is connected to and/or supported by the flex frame 110. The SM material 120 is preferably supported by (e.g., wrapped around, passed through, adhered to, etc.) one or more support regions 112 of the flex frame, but can additionally or alternatively be supported by and/or connected to an enclosed opening 114, bridge 116, terminal 117, rotation point 118, encasing 119, or any other element of the flex frame 110 or compression garment 100. The SM material 120 is preferably "loosely" connected to the flex frame 110, such that only a portion of the length of SM material 120 makes contact with the flex frame. In one variation, for instance, the SM material 120 does not make physical contact with the flex frame at or over the enclosed openings 114. Additionally or alternatively, the SM material 120 can make contact with the flex frame 110 over its entire length (e.g., when flex frame 110 includes a covering 119). The SM material 120 is preferably electrically connected to a terminal 117 of the flex frame 110 but can additionally or alternatively be directly electrically connected to a control module, a power module, or any other electronic component of the compression garment 100.

The SM material preferably includes an SM alloy (e.g., Nitinol wire) and an SM polymer (e.g., SM polymer foam, SM polymer polyurethanes, etc.), but can alternatively include one or more SM alloys, one or more SM polymers, non-SM materials (e.g., copper wire) or any combination of these or other materials.

Figure 3A:
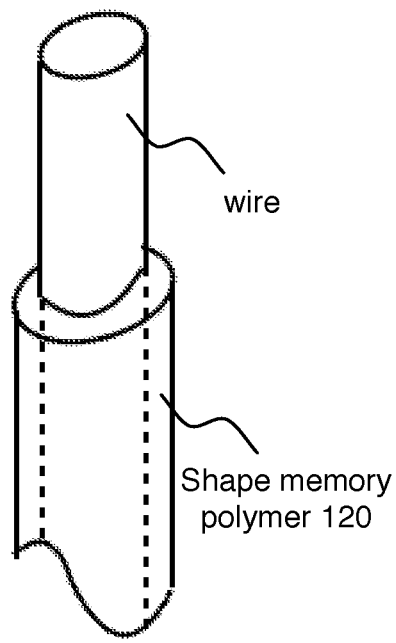
FIGS. 3A and 3B are example embodiments of a shape memory polymer as a sleeve for a wire or cable.
Figure 3B:
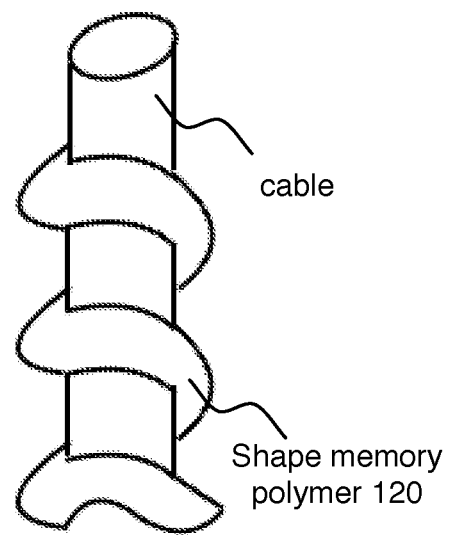
Figure 4A:
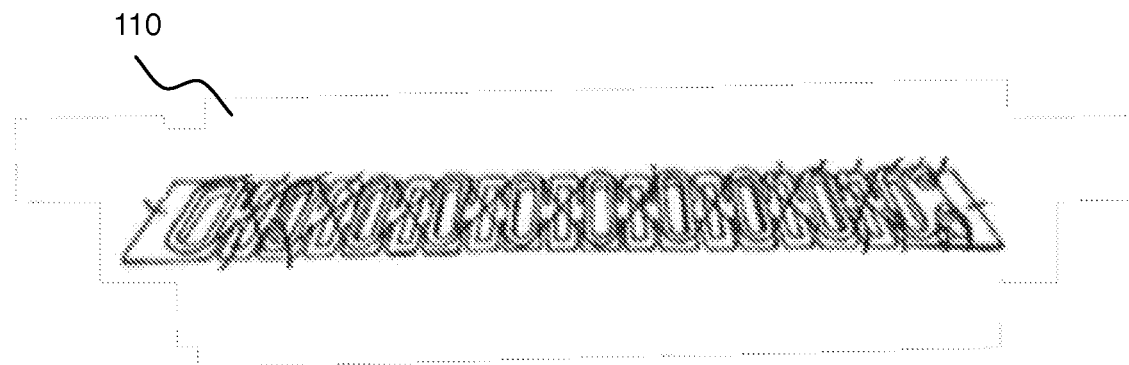
FIGS. 4A and 4B are example embodiments of a flex frame.
Figure 4B:
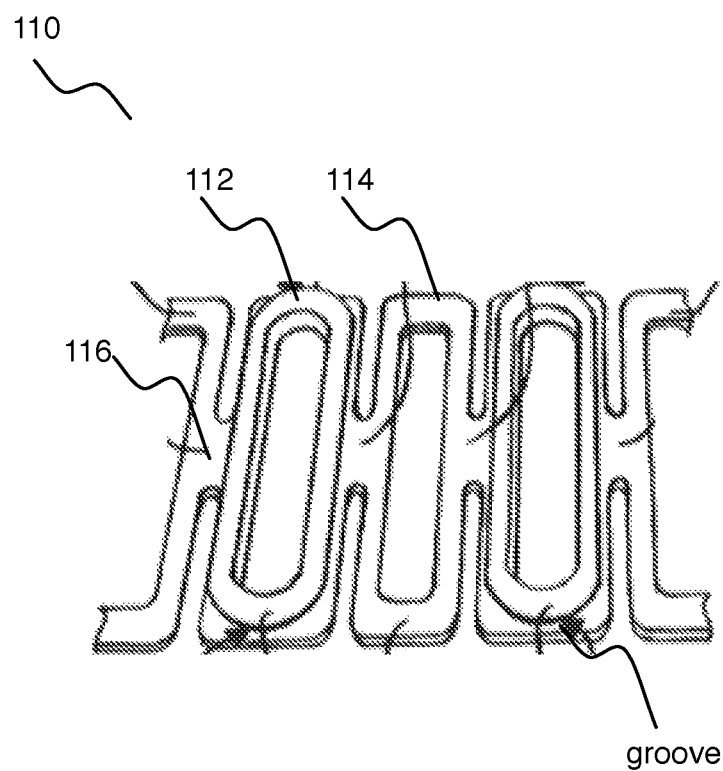
Figure 5A:
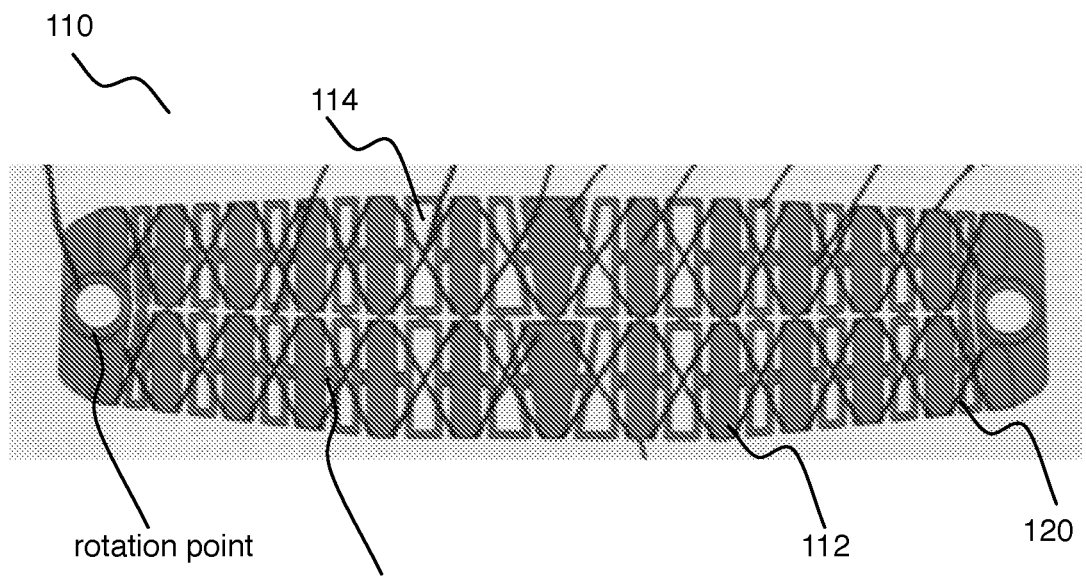
FIGS. 5A and 5B are example embodiments of a flex frame.
Figure 5B:
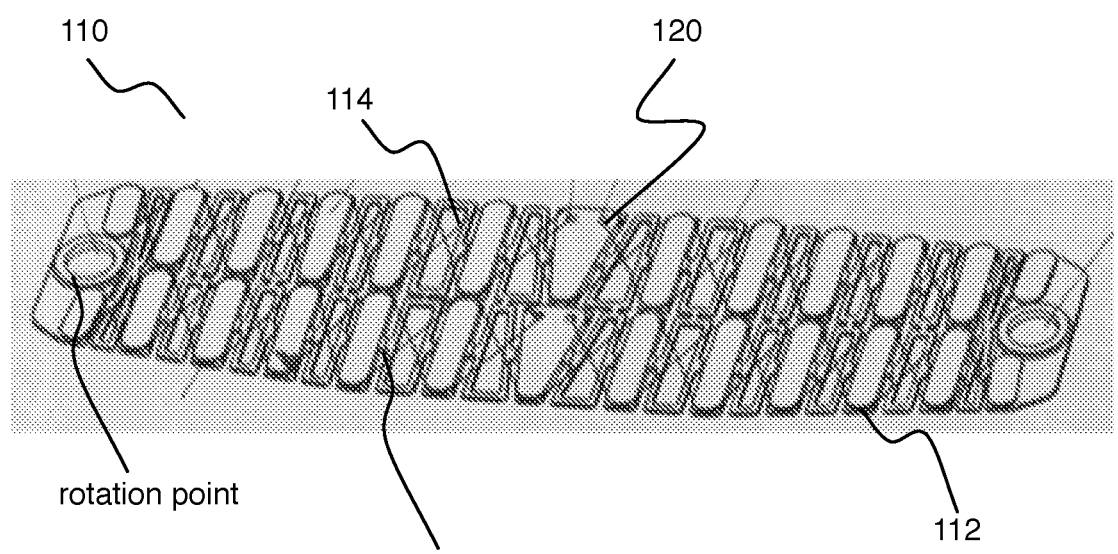

The SM material 120 preferably includes an elongated member, such as an SM alloy wire (e.g., FLEXINOL® actuator wire), ribbon, thread, or other, whereby the SM alloy material 120 is configured to wrap around components of the flex frame 110. Additionally or alternatively, the SM alloy material can include a bar, rod, film/sheet, mesh, or any other suitable configuration for applying compression to a user. The SM material 120 preferably further includes an SM polymer, the SM polymer configured to experience morphological changes (e.g., in response to morphological changes of an SM alloy). The SM alloy is preferably constructed from a nickel-titanium (Nitinol) alloy, but alternatively can be made of a copper-aluminum-nickel alloy or any other alloy (e.g., Fe—Mn—Si, Cu—Zn—Al, Cu—Al—Ni, etc.) configured to morphologically change in response to a stimulus (e.g., temperature change). The SM polymer can be in the form of an SM foam (e.g., encasing the flex frame, mounted to the flex frame, etc.), an SM sleeve (e.g., a sleeve at least partially encasing a length of SM alloy wire, a sleeve at least partially encasing a length of non-SM wire, a length of SM polymer wrapped around a length of SM alloy, etc.), or have any other suitable configuration for applying compression to a user. Preferably, the SM polymer is constructed from one or more polyurethanes, but can additionally or alternatively be constructed from any suitable material. In some variations (see FIGS. 3A-3B), SM polymer can be used as a sleeve for an SM alloy (e.g., SM wire), a non-SM wire, a magnetic wire, cable (e.g., fiber optic cable), or other material. The SM polymer can function as an insulator or can have any other suitable purpose.

Figure 13A:
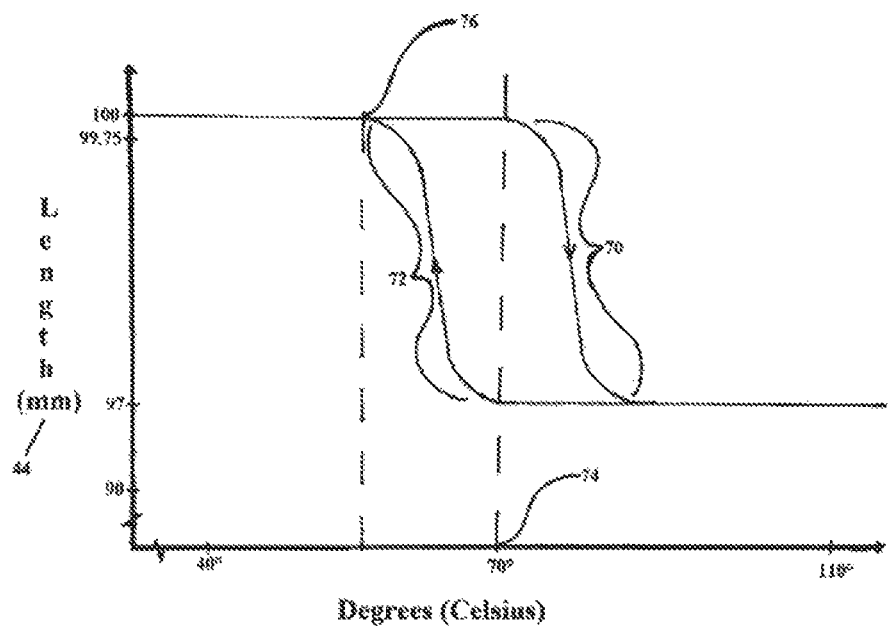
FIG. 13A depicts the heating, cooling, and standby phases of an SM material in an embodiment of the compression garment.
Figure 13B:
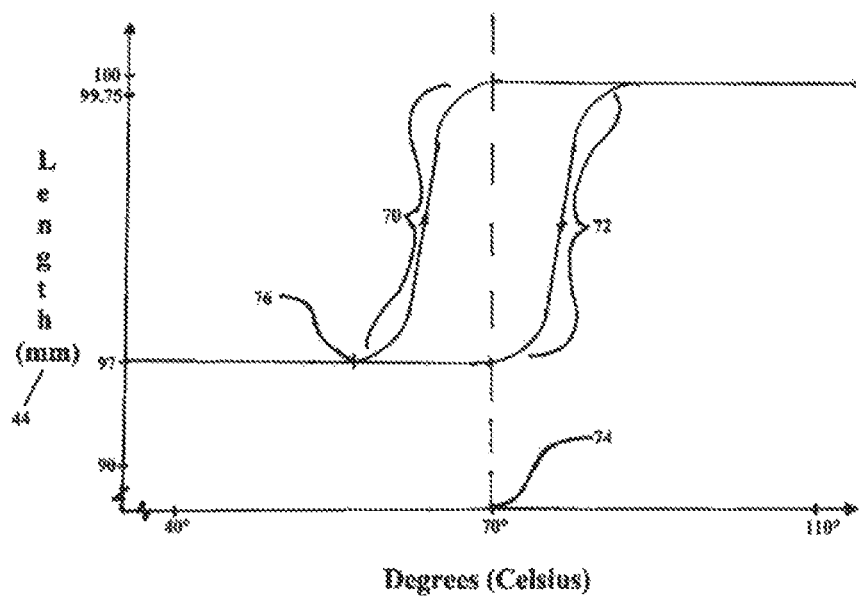
FIG. 13B depicts the heating, cooling, and standby phases of a different SM material than that of FIG. 13A, in an embodiment of the compression garment.
Figure 13C:
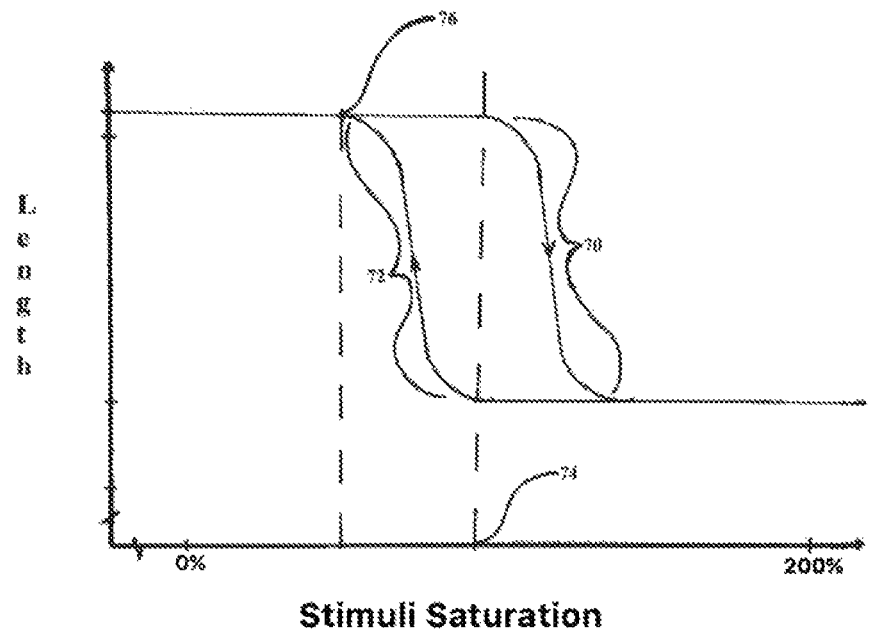
FIG. 13C depicts the reset, set, and standby phases of an SM material in an embodiment of the compression garment.
Figure 13D:
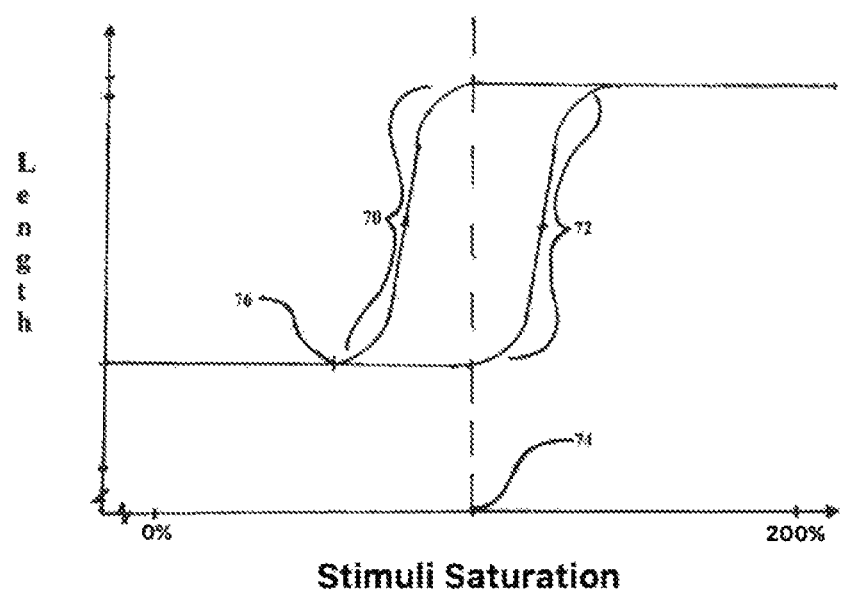
FIG. 13D depicts the reset, set, and standby phases of a different SM material than that of FIG. 13C, in an embodiment of the compression garment.

Any or all of the SM material can be a one-way SM, a two-way SM, or any other form of SM. The SM material can have two or more distinct phases/structures, which can be referred to as an austenite and a martenite phase, a deformed and an undeformed phase, a lengthened and a contracted phase, a heated and a cooled phase, and/or any other set of phases/structures. In variations having an SM alloy and an SM polymer, the SM alloy and the SM polymer can have the same set of phases and/or transition temperatures, or a different set of phases and/or transition temperature. In some variations, the SM material has a standby phase, wherein in the standby phase, the length of the shape memory material remains unchanged. The standby phase can correspond to a temperature or range of temperatures just below a predetermined threshold temperature. A transition between phases/structures of the SM material results in a morphological change to the SM material, preferably as a change in length, but additionally or alternatively a change in diameter, volume, elasticity, or any other parameter. This transition can be triggered with one or more stimuli, wherein the stimuli include a temperature change. The SM material 120 of the compression garment 100 preferably contracts in length when heated to a temperature above a predetermined threshold. The predetermined threshold is preferably approximately or exactly 72 degrees Celsius, but can additionally or alternatively be within the range of 65-75 degrees Celsius, 60-80 degrees Celsius, 0-200 degrees Celsius, or any other suitable temperature or range of temperatures. In some variations, the SM material 120 experiences a morphological change at multiple different temperature thresholds. In some variations, as shown in FIGS. 13A and 13B, the SM material can include a heating, a cooling, and a standby phase. In some variations, as shown in FIGS. 13C and 13D, the SM material can include a reset, a set, and a standby phase.

The term "heating phase" as used herein can refer to a time period during which a length of the shape memory material is warmed (e.g., in response to stimulation with an applied current, in response to passive heat transmitted from an SM alloy to an SM polymer, etc.) to reach a target transition temperature to either lengthen or shorten the shape memory material. The time period can be long or short. In some embodiments, the time period can range from 0.1 seconds to 1,000 minutes, or for example, be a time period such as 3 seconds or 3 minutes.

The term "cooling phase" as used herein can refer to a time period during which an SM material is cooled to reach a target transition temperature to either lengthen or shorten the shape memory material. The time period can be long or short. In some embodiments the time period can range from 1,000 minutes and 0.1 seconds, or for example, be a time period such as 3 minutes or 3 seconds. For the cooling phase, the SM material can either lengthen or shorten, performing a movement that is specifically opposite the movement caused during the heating phase.

The term "set phase" as used herein can refer to a time period during which an SM material is deformed from its pre-set shape. This is during the phase that the SM materials are not exposed to its stimuli. For example, SM polymer that is activated by UV light would not be exposed to UV light during its set phase. In the compression sleeve embodiment, the sleeve would have reduced pressure during this phase.

The term "reset phase" as used herein can refer to a time period during which an SM material is exposed to its stimuli. During this phase, the SM material is reverted back to its designed shape. For example, an SM polymer that is activated by UV light would be exposed to UV light. During the exposure of UV light the polymer would revert to its designed shape. The compression garment could correspondingly apply an increased compression during this phase.

The term "standby phase" as used herein can refer to the interval of time when the activation stimuli is held just below a critical threshold, such as 68 degrees Celsius for a target transition temperature of 72 degrees Celsius. In the standby phase, a length of the SM material remains unchanged. In the standby phase, the stimulus of the SM material prepares the SM material for the shortening or lengthening when an additional stimulus is applied to cross over the critical threshold.

The SM material (e.g., SM alloy) preferably contracts between 2-5% in length in response to a phase transition (e.g., reaching a predetermined temperature threshold), but can additionally or alternatively contract any suitable percentage in length. The length contraction of the SM material 120 can occur contemporaneously (e.g., in real-time, near real-time, substantially in real-time), in temporal relation (e.g., with a set delay or lag, with a random delay or lag, etc.), or in any suitable way in response to heating. Heating of the SM material 120 can be achieved in response to application of a current to the SM material 120. Additionally or alternatively, heating can be achieved through the use of a heating element (e.g., resistive heater, air-activated heating element, etc.), an external heat source, body heat of a user, or any other heat source. In some variations, a morphological change to a SM material can be induced through a stimulus other than heat, such as light. In one example, for instance, the compression garment 100 can include light-activated shape memory polymers.

In a first variation, the SM material is supported by the flex frame in a lattice arrangement. In a first specific example, for instance, the SM material (e.g., SM alloy) is wrapped from a first edge (e.g., top edge) of a first support region 112 to a second edge (e.g., bottom edge) of a second support region 112, the second support region 112 following the first support region 112, to a first edge (e.g., top edge) of a third support region, the third support region following the second support region 112, and so on down the length of the flex frame 110 (see FIG. 4A). Upon reaching the end of the flex frame 110, the SM material can wrap around the side of the last support region 112 and then travel back to the first support region 112 in the same alternating fashion, wherein the SM material can cross over itself proximal (e.g., over) the enclosed openings or anywhere else on the flex frame. In some examples, the SM material can wrap at least partially around the rotation point. In a second specific example, the SM material 120 can weave through cutouts in the enclosed openings 114. Additionally or alternatively, the SM material 120 can be arranged (e.g., woven through, wrapped around, twisted around, etc.) in any other way, to form any sort of lattice structure.

In a second variation, the SM material 120 is split into multiple separate pieces. In a first specific example, for instance, the SM material 120 includes multiple wires or bars adhered to different regions (e.g., neighboring support regions) of the flex frame 110. In a second specific example, the SM material 120 can include multiple types of SM material 120, such as an SM wire embedded in an SM polymer. Additionally or alternatively, the SM material 120 can be substituted with a non-metallic shape memory material can undergoes morphological changes in response to any other suitable type of stimulation.

In a third variation, the SM material 120 includes an SM alloy (e.g., SM alloy wire) encased in an SM polymer (e.g., SM polymer sleeve, SM polymer length wrapped around SM alloy, etc.), the combined SM alloy and SM polymer length wrapped around support regions 112 of the flex frame. In a specific example, the SM alloy contracts in response to an applied current definition and the SM polymer contracts in response to passive heat generated by the SM alloy. In a second specific example, the flex frame 110 can include an SM alloy wrapped around its support regions 112, wherein the flex frame 110 and SM alloy are both at least partially encased (e.g., mounted to on a single surface, fully encased, etc.) in an SM polymer foam. In either of these examples, the flex frame 110 can function to restore the SM polymer to an initial expanded state/phase (e.g., after a predetermined time delay, after a temperature of the SM alloy and/or SM polymer has decreased to a predetermined threshold, etc.).

In some variations, the SM material 120 includes a magnetic wire wrapped with an SM polymer (e.g., SM polymer strand) containing magnetic particles. The SM polymer with magnetic particles can be twisted and stretched around the magnetic wire, wherein the SM polymer has one or more directions of twist. In this configuration, the SM polymer can be thought of as a sleeve of the magnetic wire. When an alternating or pulsed current is run through the magnetic wire, it generates an alternating or pulsed magnetic field. The alternating or pulsed magnetic field causes the magnetic particles to vibrate and heat up. The heat stimulates the SM polymer, causing it to contract. In some examples, the SM polymer can be woven, wrapped, molded or adhered to the magnetic wire. In some examples, the SM polymer can be designed and used as an insulator (electric and thermal insulator).

In some variations, the SM material can include a fiber optic cable with light diffusion surrounded by a UV-activated SM polymer. The UV-activated SM polymer can start out as a single strand, which can be twisted and stretched around the fiber optic cable with one or more directions of twist. In this configuration, the SM polymer can be thought of as a sleeve to the fiber optic cable. When UV light is sent through the fiber optic cable with light diffusion, the UV light stimulates the SM polymer sleeve, causing it to contract. The shape memory polymer can additionally or alternatively be woven, wrapped, molded or adhered to the fiber optic cable. In some examples, the shape memory polymer can be designed and used as an insulator (light and thermal insulator).

3.9 Flexible Backing

The compression garment 100 can include a flexible backing 130, which functions to hold the flex array 110 against a user (e.g., to apply a pressure, such as a circumferential pressure, above a predetermined baseline pressure). Additionally or alternatively, the flexible backing 130 can function to protect components of the compression garment 100 (e.g., from user perspiration, spills, etc.), contribute to the durability of the compression garment 100, contour the flex frame 110 to the user, or perform any other suitable function.

The flexible backing 130 is preferably arranged exterior the flex frame 110 but can alternatively be arranged interior a part or all of flex frame 110, or in any other arrangement. The flexible backing 130 preferably contacts (e.g., is adhered to, fastened to, pressed against, etc.) an external broad surface (e.g., broad surface of the flex frame oriented away from the user) of the flex frame 110 but can additionally or alternatively contact other surfaces (e.g., the innermost surface) and/or any other suitable portion of the flex frame 110. The flexible backing 130 further preferably contacts a fabric sleeve of the compression garment 100 but can additionally or alternatively contact the user or any other component of the compression garment 100. The flexible backing 130 can be permanently connected (e.g., glued, sewn, enclosed/encased, etc.) to the flex frame 110, removably connected (e.g., press fit, strapped to, etc.) to the flex frame 110 (such as for cleaning or replacement purposes), or not connected (e.g., pressed against, held by compression, etc.) to the flex frame 110.

The flexible backing 130 is configured to at least partially wrap circumferentially around a limb (e.g., a calf region) of a user. Additionally or alternatively, the flexible backing 130 can be configured to wrap around the trunk of a user or any other part of a user's body. The flexible backing 130 preferably includes one or more strips or tabs, each arranged in a circumferential direction of the compression garment, such that the collective set of strips or tabs, when arranged (e.g., stacked) in a proximal-distal direction, spans the length of a limb. Additionally or alternatively, the flexible backing 130 can include strips or tabs each arranged in a proximal-distal direction, in a helical fashion (e.g., to wrap around and up and down a limb), no strips or tabs, or any other cutouts or features. The strips or tabs are each preferably connected to a fastener at each of its ends, the fastener configured to hold the flexible backing 130 against a user. Additionally or alternatively, each strip or tab can be collected to multiple fasteners, the set of strips or tabs can be collected to a single fastener, the strips or tabs can serve as a fastener (e.g., tie their ends together), or the strips or tabs can be arranged in any other suitable manner. The strips or tabs can function to minimize the total material used in the flexible backing, contribute to the compression garment being lightweight and portable, and/or perform any other suitable function. Preferably, the strips or tabs are joined together in a center portion (e.g., a proximal-distal center column) of the flexible backing 130 but can alternatively remain separate. The strips or tabs can be uniform or non-uniform (e.g., of different length, height, thickness, material, curvature, etc.). The strip or tab features can be designed to improve fit across a range of users or body parts, increase user comfort (e.g., include padding), improve contouring of a body part (e.g., have non-uniform lengths), minimize the compression garment size or profile (e.g., to be worn underneath clothing), or to achieve any other purpose. The strips or tabs can be inextensible (e.g., to maintain an appropriate level of compression) or extensible (e.g., to fit a wide range of user sizes).

The flexible backing 130 is preferably constructed from a compliant (e.g., soft, cushioned, etc.) material for comfort and fit purposes, such as a polymer (e.g., rubber), fabric, foam, cushion, shape memory foam or polymer. Additionally or alternatively, the flexible backing 130 can be constructed from a rigid material (e.g., molded to the user's particular geometry), such as a polymer (e.g., plastic, thermoplastic). In some variations, the flexible backing 130 is a combination of compliant and rigid materials; for example, the flexible backing can include a compliant material on the inner surface for user comfort and a right material on the outer surface for durability and structure. The flexible backing 130 can be solid, perforated (e.g., with ventilation holes for breathability), or hollow (e.g., to reduce materials/weight for increased comfort/portability). Additionally or alternatively, the flexible backing 130 can include channels and/or pockets (e.g., to retain a coolant, retain a heating fluid, hold a heating element, permit air flow, etc.). The flexible backing can be constructed through molding (e.g., injection molding), 3D-printing, vacuum forming, die-cutting, sewing, or any other process. In one variation, the flexible backing 130 includes a fabric sheet with strips cut out from the sides.

Figure 9:
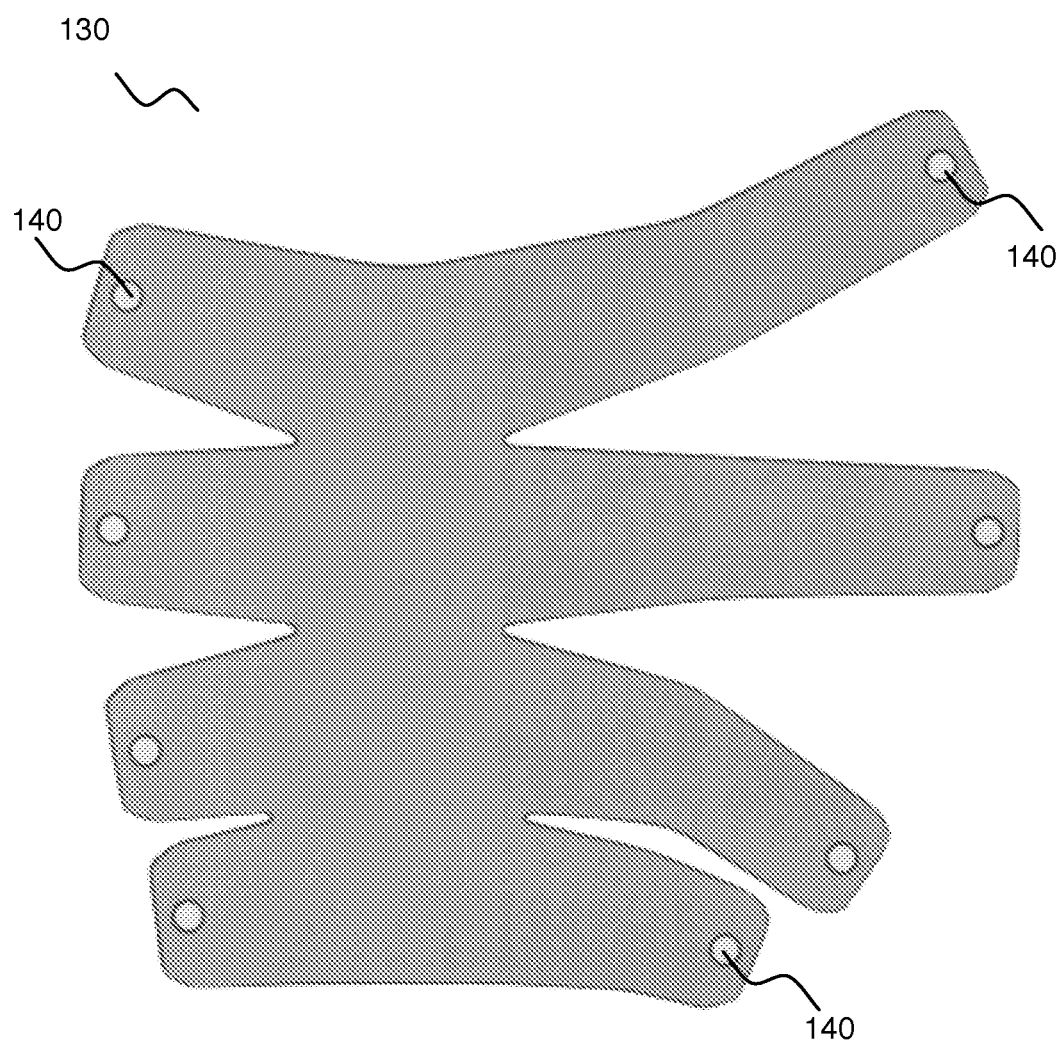
FIG. 9 is an example embodiment of a flexible backing having a series of strips.
Figure 12:
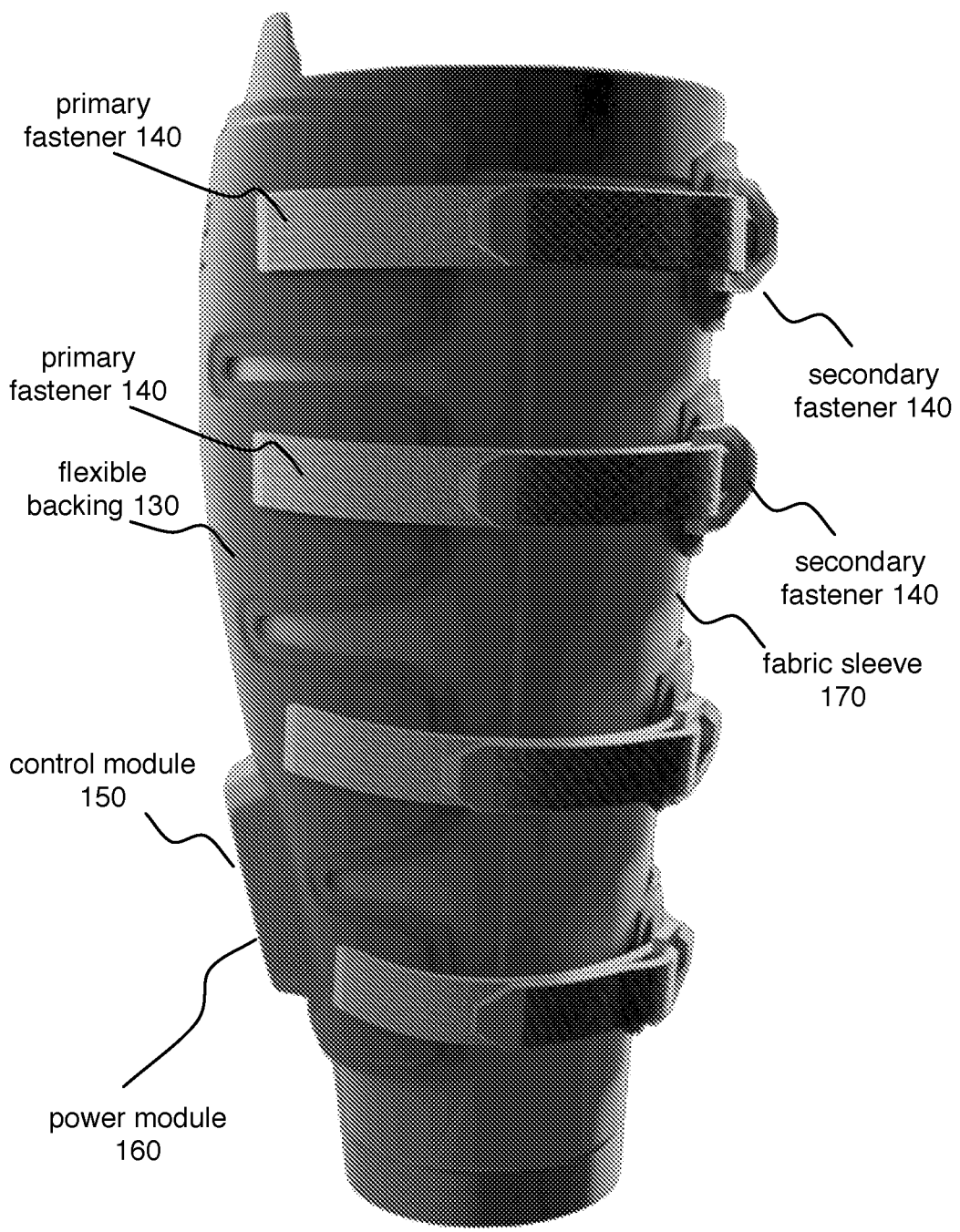
FIG. 12 is an example embodiment of a compression garment having a dual fastener system.

In a first variation, as seen in FIG. 9, the flexible backing 130 includes a series of strips arranged in a proximal-distal direction, wherein the strips converge in a central portion of the flexible backing 130. In a specific example, as shown in FIG. 12, the strips each include a fastener attached to the strip end, the fastener configured to hold the two ends of the strip together. As shown in FIGS. 9 and 12, the strips can have non-uniform lengths (e.g., proximal strips are longer than distal strips) as well as curvature to better contour a limb of the user, such as a calf region.

In a second variation, the flexible backing 130 is a flexible sleeve (e.g. spandex or elastic fabric), which can be arranged over one or more flex frames and hold them against the user through passive compression. In a first specific example, the flexible sleeve is attached to the user through fasteners arranged to hold two ends of the flexible sleeve together. In a second specific example, the flexible sleeve does not include fasteners and is configured to be stretched and slipped over a limb of the user.

Figure 11:
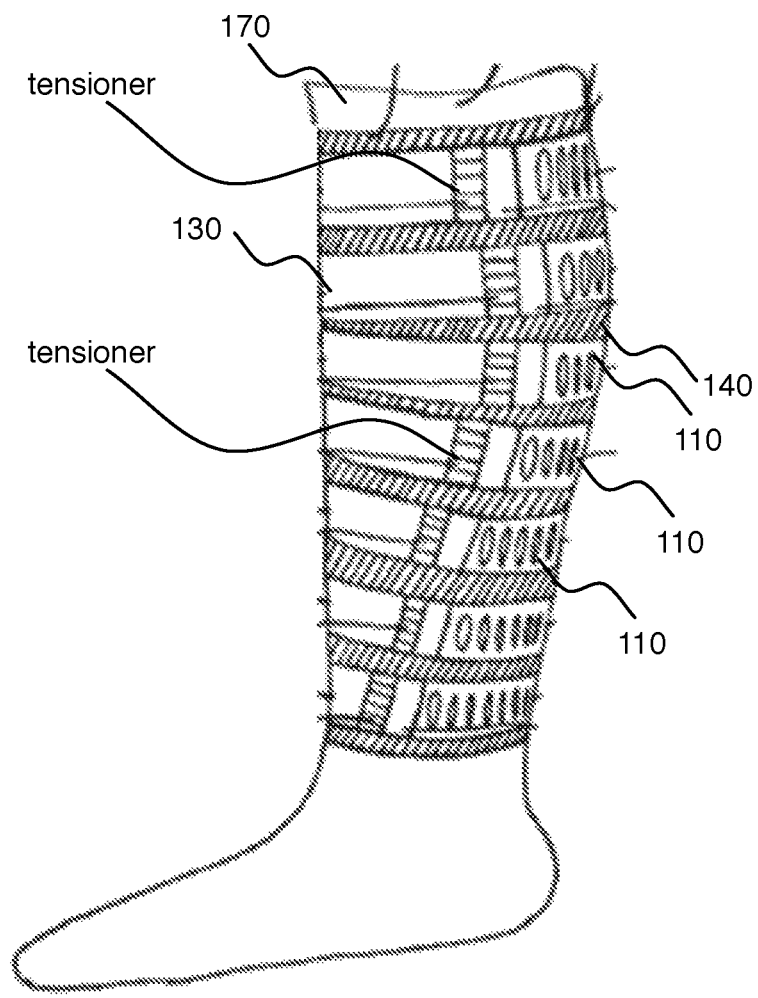
FIG. 11 is an example embodiment of a compression garment arranged on the leg of a user.

In a third variation, the flexible backing 130 includes a set of tensioners (e.g., FIG. 11), wherein the tensioners can be configured to hold a plurality of flex frames together, to attach one or more flex frames no to the flexible backing 130, to hold SM material 120 in tension, or to perform any other function. In a first specific example, the set of tensioners includes a set of bands (e.g., elastic bands) arranged between adjacent flex frames, wherein the tensioners hold the flex frames together. In a second specific example, a tensioner (e.g., band, loop, fastener, etc.) is arranged between an inner surface of the flexible backing 130 and each end of a flex frame 110, wherein the tensioners are configured to hold the flex frame 110 and to keep it in a state of tension.

3.10 System—Fastener

The compression garment 100 preferably includes one or more fasteners 140, which can function to hold the flexible backing 130 on a user. Additionally or alternatively, the fastener 140 can function to hold a flex frame 110 on a user, apply a passive compression (e.g., to enhance circulation) to a limb of a user, or perform any other suitable function.

Preferably, one or more fasteners 140 is connected to the flexible backing 130. In one variation, a set of fasteners 140 is used to hold two ends of the flexible backing 130 together. In a first specific example, the set of fasteners 140 (e.g., straps, strings, etc.) holds the two ends together at a distance. In a second specific example, the set of fasteners 140 holds two ends of the flexible backing 130 together in contact, such as through a lacing, zipper, etc. In a second variation, a set of fasteners 140 holds two ends of the flexible backing 130 together in an overlapping configuration, such as with straps, hook-and-loop fasteners (e.g., Velcro) arranged between the overlapping layers, magnetic strips, buttons, closed cell thin foam, tape or straps wrapped circumferentially around the flexible backing, etc. Additionally or alternatively, one or more fasteners 140 can be connected to a flex frame 110 or any other component of the compression garment 100.

Preferably, the fastener system 140 is a dual fastener system, having a first fastener 140 for sizing and a second fastener 140 for placement and removal of the compression garment 100. This arrangement, for instance, can allow the user to use the first fastener 140 (e.g., straps and buckles) to set a repeatable sizing of the device (e.g., during an initial use/set-up of the compression garment) and use the second fastener 140 (e.g., hook and loop system) to take the compression garment on and off without adjusting the sizing set by the first fastener 140. The first fastener 140 is preferably configured for multiple different configurations and sizes of user, such as a hook-and-loop fastener (e.g., Velcro) strap, elastic band, multi-notch belt, lacing, etc., but can additionally or alternatively be configured for any other function. The second fastener 140 is preferably configured for easy placement and removal of the compression garment 100 on a user, such as a snap, button, magnet, hook and loop, etc., but can additionally or alternatively be configured for any other function. In some variations, the first and second fasteners 140 are the same type of fastener and/or the same fastener.

In one variation, the fastener 140 includes a set of hook-and-loop fastener (e.g., Velcro) straps arranged at an end of each of the strips of a flexible backing 130. In this variation, the fastener 140 further includes a loop (e.g., plastic rectangular loop) moveably arranged along the length of each hook-and-loop fastener (e.g., Velcro) strap. During set-up/initial use of the compression garment 100, the user can fold over and secure an end of the hook-and-loop fastener (e.g., Velcro) strap to a desired position along its length, thereby setting the size of the device and the position of the loop along the length of the strap. A hook or post on the opposing end of the strip serves as a second fastener 140 along with the loop, wherein the user can attach and remove the device using this second fastener 140 (securing the loop over the hook or post), without having to adjust the sizing determined by the first fastener (Velcro strap).

In another variation, the fastener 140 can include one or more straps (e.g., Velcro straps), which wrap around the entire circumference of the body part of the user to which the compression garment 100 is applied.

3.11 System—Control Module

The compression garment 100 preferably includes a control module 150, such as a controller in communication with a stimulus generator, which functions to provide current definitions (e.g., current levels, timing) for application of a current definition to the SM material for treatment. Additionally or alternatively, the control module 150 can function to apply current for heating the SM material, store stimulation patterns, share stimulation patterns (e.g., between users through an application on a user device, the cloud, etc.), monitor device performance, implement a fail-safe (e.g., power shut-off in the event of overheating, alarm, etc.) using a sensor system, or perform any other suitable function.

The control module 150 is electrically connected to the SM material. The control module 150, at least in part, is preferably attached to (e.g., mounted to, placed within, adhered to, sewn to, sewn within, etc.) the flexible backing 130 but can additionally or alternatively be attached to a flex frame 110, fabric sleeve, or any other component of the compression garment 100. In some variations, the control module 140 is electrically connected to a heating element (e.g., a resistive heater). The control module 140 can be wirelessly coupled to an external device, such as a user device. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi module, BLE, cellular module, etc.), or any other suitable component.

Figure 10:
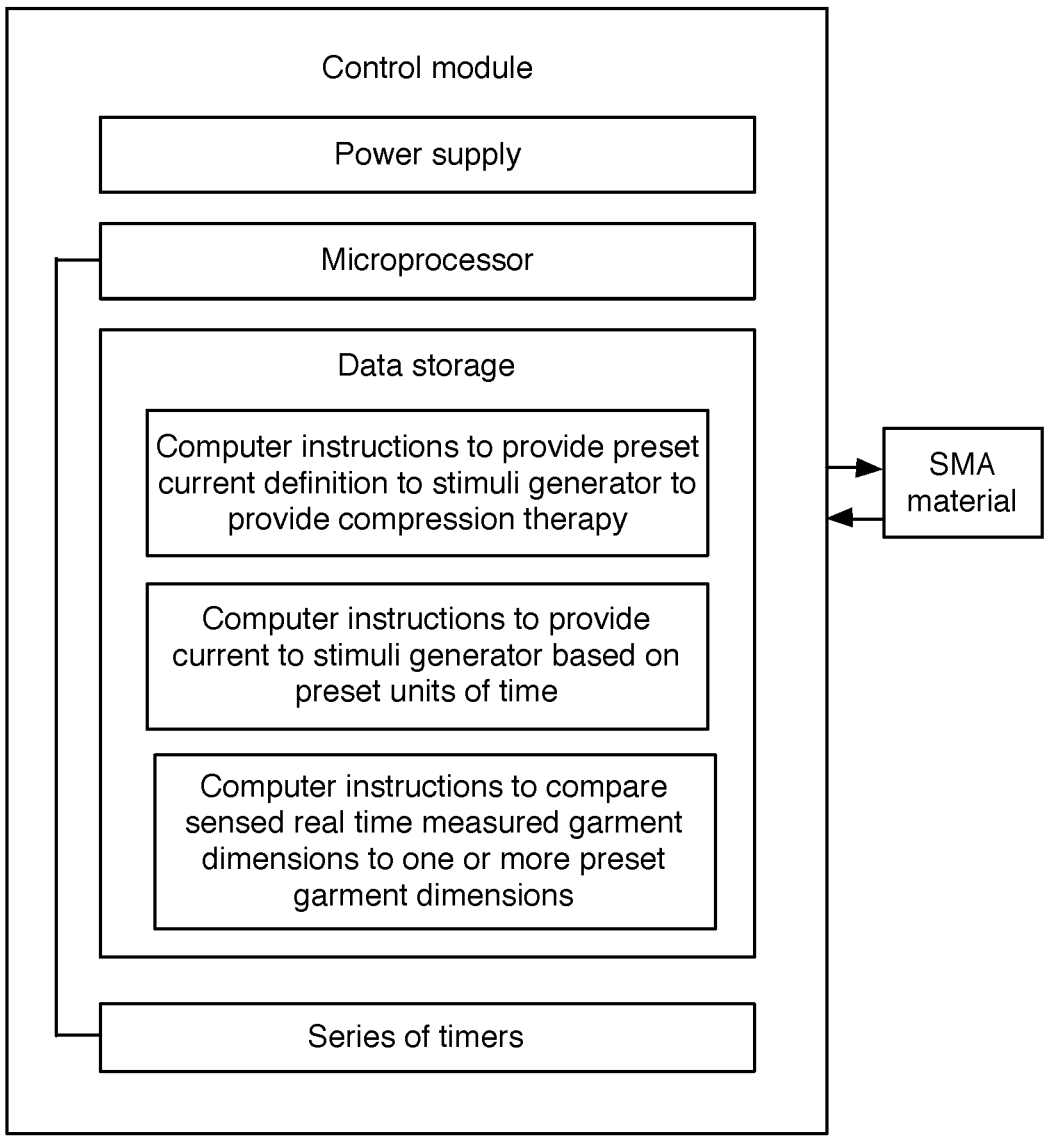
FIG. 10 is a schematic depiction of applying a current definition to a shape memory (SM) material.

The control module 150 preferably includes one or more of: a controller (e.g., a microcontroller), processor (e.g., a microprocessor), system on a chip (SoC) or other integrated circuit, timing subsystem including a set of timers (e.g., FIG. 10), and/or stimulus generator (e.g., multi-channel stimulus generator, set of stimulation control instructions, etc.), but can additionally or alternatively include any other circuitry, electronic component, or control unit configured to elicit a morphological change (e.g., apply a current definition) in the SM material.

In some variations, the control module 150 can include a stimulus generator (e.g., FIG. 10), which functions to transmit a current definition to the SM material and/or any other component of the compression garment 100. Additionally or alternatively, the stimulus generator can function to apply other stimuli, such as, but not limited to: an electric field, magnetic field, ultraviolet (UV) light, heat, water, and/or any other stimuli. The stimulus generator can be electrically coupled to the SM material, other elements of the control module 150, and/or a power module of the compression garment 100. The stimulus generator preferably comprises a current generator, but can additionally or alternatively include a voltage generator and/or any other suitable generator configured to facilitate transmission of a current definition and/or any other form of electrical stimulation. As such, the stimulus generator can provide one or more current definitions, such as a direct current (DC), an alternating current (AC), an AC component superimposed on a DC component, a monophasic pulsatile waveform, a symmetrical biphasic pulsatile waveform, an asymmetrical biphasic pulsatile waveform, and any other suitable stimulation profile. The waveform produced by the stimulus generator preferably can be described by parameters comprising amplitude and duration, but additionally or alternatively comprising any other suitable parameter(s), such as modulation frequency, step size, mean amplitude, or root mean squared (RMS) value. Furthermore, any one or more of the above parameters can be configured to be modulated by the stimulus generator, such that the stimulus generator can produce any one or more of: modulated amplitudes, modulated frequencies, and modulated pulse durations (e.g., modulated parameters characterized by exponential decay, exponential growth, or any other suitable growth or decay profiles). While one stimulus generator is described, the control module can, in some variations, comprise more than one stimulus generator (e.g., a separate stimulus generator for each flex frame), where the control module is configured to multiplex output of the additional stimulus generators to one or more flex frames 110 or subsections thereof.

In one variation, the stimulus generator functions to increase the temperature of an SM material through the application through an alternating or pulsing magnetic field. In a specific example, for instance, the applied magnetic field can interact with magnetic particles of the SM material causing the magnetic particles to vibrate, thereby increasing the temperature of the SM material 120. In a second specific example, an applied current definition (e.g., pulsing current definition) to a wire (e.g., helically arranged wire, SM alloy wire, etc.) can create a magnetic field (e.g., pulsing magnetic field), wherein the magnetic field interacts with magnetic particles of the SM polymer material, causing the magnetic particles to vibrate and therefore increase the temperature of the SM polymer material.

In a second variation, the stimulus generator can include an SM alloy, wherein the SM alloy functions to generate a heat stimulus for an SM polymer.

The control module 150 can include data storage (e.g., to store stimulation patterns), which can be onboard the compression garment (e.g., in the form of a memory chip, memory card, etc.) or external to the compression garment (e.g., via wireless communication with a remote server, the cloud, etc.).

The control module 150 can also include a sensor system mounted to or integrated within any part of the compression garment (e.g., attached to the flexible backing). The compression garment can, for instance, include any one or more of: a moisture sensor, pressure sensor, contact sensor, optical sensor (e.g., light sensor, camera, etc.), orientation sensor (e.g., accelerometer, gyroscope, altimeter, etc.), audio sensor (e.g., microphone), or any other sensor. The sensor system can be used to implement fail-safes (e.g., activate alarm based on temperature sensor data), determine/trigger operational modes, or can be used for any other purpose. In some variations, the control module 140 further includes one or more wireless communication components, such as an antenna, WiFi chip, Bluetooth chip, or any other component.

The control module (e.g., stimulus generator, controller and stimulus generator) 150 is preferably configured to apply one or more stimulus patterns to the SM material. The stimulation pattern preferably includes a current definition, wherein the current definition can include (or correspond to, be based on, etc.) any or all of a current amplitude (e.g., a static current amplitude, a maximum current amplitude, a minimum current amplitude, etc.), a current waveform (e.g., sinusoidal, ramp, step, square, triangular, etc.), or any other form of current-related parameter. Additionally or alternatively, the stimulation pattern can include a voltage definition, power definition, heating command, or any other form of stimulus. The stimulation pattern can further include temporal parameters, such as, but not limited to: a duration of a stimulus pattern, a sequence of stimulation patterns (e.g., ramp-up followed by static hold), time of onset (e.g., apply a specified current definition at a specified time each day, upon detection of compression garment placement on a user, etc.), a frequency of a current waveform, and/or a speed of propagation of a current definition. In some variations, the temporal parameters are determined using a timing subsystem including a set of timers). In some variations, a stimulation pattern or a set of stimulation patterns can be applied which dynamically propagate compression in a specified direction (e.g., from a distal end to a proximal end of the calf). In some variations, stimulation patterns can be applied which propagate compression in multiple directions, in a random direction, only apply a static compression, or apply any other stimulation pattern at any part of the user. In one variation, each of a series of flex frames 110, or more specifically the SM material connected to these flex frames, can be independently controlled by the control module 150. This can be implemented through a separate control module for each flex frame or piece of SM material, a single control module having separate ports for each flex frame or piece of SM material, or any other combination or configuration of single or multiple control modules. Alternatively, only a subset of flex frames 110 can be independently controlled or all of the flex frames 110 can be controlled together.

The control module 150 can operate in operation modes, each of which preferably includes a current definition and a temporal parameter. Additionally or alternatively, the operation modes can include an on/off state, any form of stimulation pattern, only one of a current definition and a temporal parameter, or any other feature of compression garment operation. Operation modes can be assigned and/or activated by a user (e.g., user makes selection through application on user device, sensor system of compression garment detects a user voice command, user presses button on a control panel of the flexible backing, etc.), based on sensor data (e.g., pressure sensor detects when device has been placed on user), based on learned behavior of user (e.g., based on machine learning of user preferences and patterns), or based on any other input. The operation modes of the control module preferably at least include a first operation mode corresponding to a first phase of the SM material (e.g., lengthened phase) and a second operation mode corresponding to a second phase of the SM material (e.g., contracted phase). In one example of this, for instance, the first operation mode prescribes a current definition that results in an SM material temperature below a predetermined threshold (e.g., below 72 degrees Celsius) and the second operation mode prescribes a current definition that results in an SM material temperature above a predetermined threshold (e.g., above 72 degrees Celsius). In another example, the first operation mode applies no current to the SM material. Additionally or alternatively, the control module can include additional operation modes, a single operation mode, an on/off operation mode, or any other operation mode.

In a first variation, the control module 150 includes an active operation mode, wherein in the active operation mode, a controller of the control module applies a threshold current definition (e.g., one that causes the SM material to reach or surpass a threshold temperature), wherein the SM material, in response to the threshold current definition, transitions from a first length to a second length, the second length smaller than the first length. In a first specific example of this, a microprocessor of the control module includes the active operation mode and an 'off' operation mode, wherein a transition from 'off' to 'active' results in a contraction in length of the SM material and a transition from 'active' to 'off' results in an extension in length of the SM material.

Additionally or alternatively, in a second variation, the control module 150 is configured to independently control the morphological changes to each of a series of flex frames 110. In a specific example, for instance, the compression garment 100 includes a series of flex frames 110 arranged along a proximal-distal axis of the compression garment. Through independent control of the SM material in each of the flex frames 110 (e.g., through separate microprocessors), stimulation patterns can be applied which propagate up and down a limb of the user (e.g., in a cyclical fashion).

In a third variation, the control module 150 is mounted to the flexible backing 130. In a first specific example, the flexible backing 130 includes a housing (e.g., molded to protrude from an external surface of the flexible backing), wherein any or all of the control module components are enclosed in the housing. In a second specific example, the control module is arranged between layers of flexible backing 130 material.

In a fourth variation, the compression garment 100 further includes a control panel (e.g., on an external surface of the flexible backing 130), wherein the user can make operation mode selections using input devices associated with the control panel. In a first specific example, the control panel includes an on/off switch. In a second specific example, the control panel includes a set of buttons which the user can depress to make operation mode selections. In a third specific example, the control panel includes a display (e.g., a touch screen display).

In a fifth variation, the compression garment 100 can include a series of flex frames, wherein each of the flex frames is independently controllable by the control module. In a specific example, the user can select which regions of the compression garment he would like to apply compression. In another specific example, the user can select how quickly he would like a compression pulse to travel up and down his calf.

3.12 System—Power Module

The compression garment 100 can include a power module 160, which functions to enable the application of a current definition to the SM material. Additionally or alternatively, the power module 160 can function to enable the application of any stimulation pattern to the SM material, to power a control module or any other component of the compression garment 100, or to perform any other suitable function.

The power module 160 is preferably electrically connected to the control module 150 (e.g., a microprocessor), but can additionally or alternatively be electrically connected to the SM material or any other electronic component of the compression garment. The power module 160 can also be mechanically connected to any component of the compression garment, such as mounted to the flexible backing, attached to the flex frame, etc.

The power module 160 can include a power source, such as a portable power source (e.g., rechargeable battery pack, solar powered battery, etc.). Additionally or alternatively, the power module 160 can include one or more adapters to external power sources, such as a plug for a wall outlet, a cable (e.g., USB cable, extendable USB cable), a connection to a vehicle power source (e.g., plug for a car cigarette lighter receptacle, connection to a vehicle USB port, etc.), and/or any other plug, adapter, or converter.

In a first variation, the power module 160 is a pocket unit configured to be placed in a pocket of the user. In an example, for instance, the power module 160 is a rechargeable battery pack attached to the compression garment with a cable such that the battery pack can be placed in the pocket of a user. In another example, the power module 160 is a rechargeable battery back that removably couples, e.g. through a pocket or clip, to the compression garment (e.g., a pocket on an external surface of the flexible backing).

In a second variation, the power module 160 has a cigarette lighter receptacle plug, so that a user can use the compression garment and/or charge the compression garment while driving or riding in a vehicle.

3.13 Fabric Sleeve

In some variations, the compression garment 100 includes a fabric sleeve 170, which functions to apply passive compression. Additionally or alternatively, the fabric sleeve 170 can function to provide comfort to a user, protect a user from electronic components, protect electronic components from the environment or user (e.g., perspiration of a user), allow non-washable aspects of the compression garment 100 (e.g., flex frame, SM material, control module, etc.) to be separated from the user by a washable component (e.g., fabric sleeve), or to perform any other suitable function.

The fabric sleeve 170 is preferably arranged over/around the limb of a user such that the fabric sleeve is arranged internal (e.g., closer to the user) the remaining components of the compression garment 100 but can additionally or alternatively be placed on or around any other part of the user an in any relation to the other components of the compression garment. The fabric sleeve can be stretched over a limb of the user, wrapped around a limb and secured using ties or fasteners, placed on top of the user, and/or placed or secured in any suitable way. The fabric sleeve 170 can be flexible (e.g., to contour to a body part of the user, stretch over distal body parts to reach proximal body parts, fit users of multiple sizes, apply passive compression, etc.), soft and comfortable against the user's skin, compressive (e.g., to apply passive compression), thin (e.g., to propagate active compression to the user), insulative (e.g., to protect the user from heat and/or electronic components), or have any other feature. The fabric sleeve 170 can be constructed from nylon, polyester, cotton, spandex, closed cell thin foam, foam, any combination of natural and synthetic fibers, or any other suitable material.

In one variation, the fabric sleeve 170 is stretched over a limb (e.g., calf region) of the user with the flex frame and flexible backing layered over the fabric sleeve. In a first specific example, the fabric sleeve is a spandex sleeve. In a second specific example, the fabric sleeve is a strip of fabric (e.g., closed cell thin foam) wrapped around the limb of the user.

Figure 2:
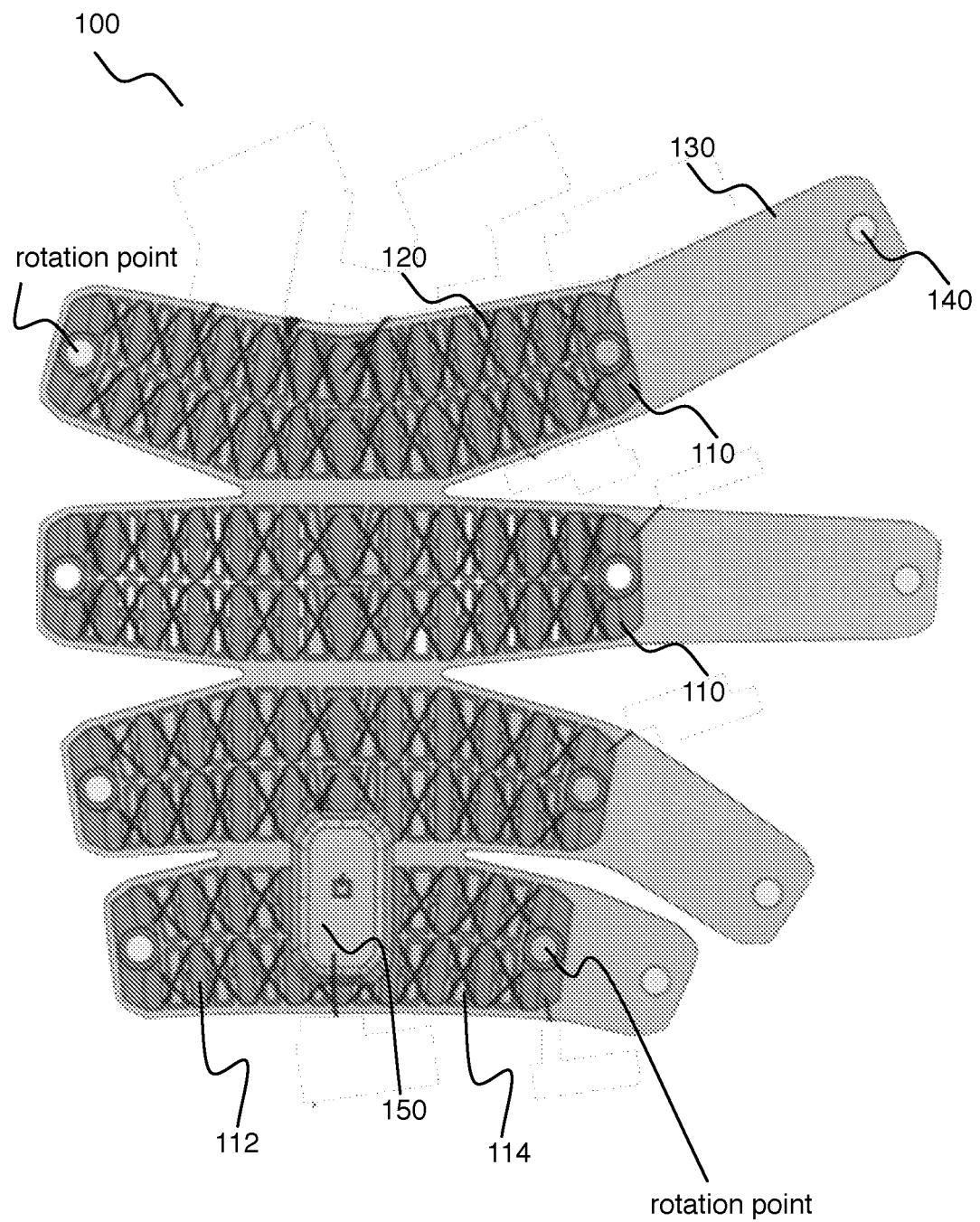
FIG. 2 is an example embodiment of a flexible backing and series of flex frames.

In a first variation of the compression garment 100, the compression garment 100 is applied to a calf of the user. In a first specific example, as shown in FIG. 2, the compression garment 100 includes a series of flex frames 110, each of the flex frames 110 further including a series of protruding (e.g., raised) support regions 112 arranged in two rows along the length of the flex frame 110 in an alternating fashion with a series of enclosed openings 114. A single wire of SM material is wrapped around the support regions 112 in a lattice arrangement. In this example, each of the flex frames 110 is a physically coextensive frame of unitary construction (e.g., formed through an injection molding process). The series of flex frames 110 are arranged in a proximal-distal direction (e.g., along the height) along an internal surface of a flexible backing 130. In this example, the flexible backing 130 includes four strips of flexible material which converge in the center. The flexible backing 130 is wrapped around the calf of the user and secured using a dual-fasteners system, wherein the first fastener (e.g., Velcro straps) is used for sizing of the compression garment and the second fastener (e.g., hook and loop fastener) is used to attach the compression garment 100 to the user. A controller 150 is arranged in the flexible backing to apply current definitions to the SM wire.

In a second specific example of the first variation, the compression garment 100 further includes a fabric sleeve 170 (e.g., a polyester sleeve) layered internally to the flex frames 110 and flexible backing 130, wherein the fabric sleeve stretches over the foot of the user and 'hugs' the calf of the user once released.

In a second variation, the compression garment 100 is applied to an arm (e.g., forearm) of a user.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A compression garment, comprising:
    a fabric sleeve;
    a flex frame arranged at an exterior surface of the fabric sleeve, the flex frame defining a broad surface and comprising:
        a series of protruding regions each having a first thickness in a proximal-distal direction, wherein a thickness of the flex frame is greatest at each of the series of protruding regions, wherein the series of protruding regions comprises a first set of grooves arranged at first edges of the series of protruding regions and a second set of grooves arranged at second edges of the series of protruding regions, and wherein the series of protruding regions comprises magnetic elements disposed at the first and the second edges;
        a series of enclosed openings each having a second thickness in the proximal-distal direction, each of the series of enclosed openings passing orthogonally through the broad surface of the flex frame, the series of enclosed openings arranged in an alternating sequence with the series of protruding regions; and
        a series of bridges of unitary construction with the series of protruding regions and the series of enclosed openings, each of the series of bridges having a bridge thickness in the proximal-distal direction that is smaller than the first thickness and the second thickness and coupling adjacent protruding region-enclosed opening pairs of the series of protruding regions and the series of enclosed openings;
    a first body of shape memory material, the first body of shape memory material comprising a shape memory alloy retained at the first set of grooves and the second set of grooves in a crossed arrangement, wherein the magnetic elements disposed at the first and the second edges of the series of protruding regions are configured to provide magnetic fields to retain the first body of shape memory material in the first and the second set of grooves;
    a second body of shape memory material comprising a shape memory polymer coupled to at least one of the first body of shape memory material and the flex frame;
    a controller comprising a microprocessor, the controller electrically connected to at least one of the first body of shape memory material and the second body of shape memory material and comprising an active mode, wherein in the active mode
    the controller applies a threshold current definition to at least one of the first and the second bodies of shape memory material and, in response, the body of shape memory alloy transitions from a first length to a second length, the second length smaller than the first length;
    a flexible backing coupled to an exterior surface of the flex frame; and
    a dual fastener system comprising a first fastener and a second fastener, the first fastener configured to be adjusted to set a custom default size for the compression garment, and the second fastener configured to be fastened to secure the compression garment on a user and unfastened to facilitate removal of the compression garment from the user without adjusting the first fastener.

2. The compression garment of claim 1, wherein the first body of shape memory material crosses over itself proximal each of the series of enclosed openings.

3. The compression garment of claim 1, further comprising a connection from the controller to a vehicle power source.

4. The compression garment of claim 1, wherein the controller is configured to apply a set of stimulation patterns, wherein each of the set of stimulation patterns comprises a current parameter for manipulation of at least one of the first and the second bodies of shape memory material in the active mode and a temporal parameter associated with the current parameter.

5. The compression garment of claim 4, wherein the compression garment comprises a first flex frame and a second flex frame, the first and second flex frames controlled independently of each other, and wherein one of the set of stimulation patterns comprises a time delay between application of a current definition to the first flex frame and application of the current definition to the second flex frame.

6. The compression garment of claim 1, wherein the shape memory polymer at least partially surrounds the shape memory alloy, the shape memory polymer comprising an expanded state and a compressed state, wherein a transition from the expanded state to the compressed state occurs in response to a predetermined temperature change of the shape memory alloy.

7. The compression garment of claim 1, wherein the second body of shape memory material comprises a set of magnetic particles, wherein an applied magnetic field induces a morphological change in the second body of shape memory material.

8. A compression garment, comprising:
a fabric sleeve; and
a flex frame arranged at an exterior surface of the fabric sleeve, the flex frame defining a broad surface and comprising:
- a series of support regions each having a first thickness in a proximal-distal direction, each of the series of support regions comprising magnetic elements disposed at a first end and a second end, wherein the magnetic elements are configured to provide magnetic fields to retain a body of shape memory material at the first and the second ends;
- a series of enclosed openings, each of the series of enclosed openings having a second thickness in the proximal-distal direction and passing orthogonally through the broad surface of the flex frame, the series of enclosed openings arranged in an alternating sequence with the series of support regions;
- a series of bridges of unitary construction with the series of support regions and the series of enclosed openings, each of the series of bridges having a bridge thickness in the proximal-distal direction smaller than the first thickness and the second thickness and coupling adjacent support region-enclosed opening pairs of the series of support regions and the series of enclosed openings; and
- a dual fastener system comprising a first fastener and a second fastener, the first fastener configured to be adjusted to set a custom default size for the compression garment, and the second fastener configured to be fastened to secure the compression garment on a user and unfastened to facilitate removal of the compression garment from the user without adjusting the first fastener.

9. The compression garment of claim 8, further comprising:
- a body of shape memory material comprising at least one of a shape memory alloy and a shape memory polymer, at least part of the body of shape memory material retained by the series of support regions in a crossed arrangement along a length of the flex frame; and
- a controller comprising a microprocessor, the controller electrically connected to the body of shape memory material and comprising an active mode, wherein in the active mode:
  - the controller applies a threshold current definition to the body of shape memory material and, in response, the body of shape memory material transitions from a first length to a second length, the second length smaller than the first length.

10. The compression garment of claim 9, further comprising a flexible backing coupled to an exterior surface of the flex frame.

11. The compression garment of claim 9, wherein the body of shape memory material comprises the shape memory alloy retained by the series of support regions in a crossed arrangement along the length of the flex frame, and wherein the body of shape memory material further comprises the shape memory polymer surrounding one or both of the shape memory alloy and the flex frame.

12. The compression garment of claim 11, wherein the shape memory polymer comprises a first morphological state and a second morphological state, wherein a transition from the first morphological state to the second morphological state is induced by a morphological change to the shape memory alloy.

13. The compression garment of claim 8, wherein a thickness of the flex frame is greatest at each of the series of support regions.

14. The compression garment of claim 8, wherein the series of support regions comprises a first set of grooves arranged at first edges of the series of support regions and a second set of grooves arranged at second edges of the series of support regions.

15. The compression garment of claim 9, wherein a segment of the body of shape memory material crosses over itself proximal each of the series of enclosed openings.

16. The compression garment of claim 9, further comprising a connection from the controller to a vehicle power source.

17. The compression garment of claim 9, wherein the controller is configured to apply a set of stimulation patterns, wherein each of the set of stimulation patterns comprises a current parameter for manipulation of a segment of the body of shape memory material and a temporal parameter associated with the current parameter.

18. The compression garment of claim 17, further comprising a biometric sensor subsystem, coupled to the controller, that generates a biometric dataset for a user, and wherein at least one of the current parameter and the temporal parameter is determined based on the biometric dataset of the user.

19. The compression garment of claim 17, wherein the compression garment comprises a first flex frame and a second flex frame, the first and second flex frames controlled independently of each other, and wherein one of the set of stimulation patterns comprises a time delay between an application of a current definition to the first flex frame and the application of the current definition to the second flex frame.

* * * * *